United States Patent [19]

Wilson et al.

[11] 4,385,994
[45] May 31, 1983

[54] ADSORPTIVE USE OF CRYSTALLINE METALLOPHOSPHATE COMPOSITIONS

[75] Inventors: Stephen T. Wilson, Shrub Oak; Brent M. Lok, New York; Edith M. Flanigen, White Plains, all of N.Y.

[73] Assignee: Union Carbide Corporation, Danbury, Conn.

[21] Appl. No.: 315,055

[22] Filed: Oct. 26, 1981

Related U.S. Application Data

[62] Division of Ser. No. 166,333, Jul. 7, 1980, Pat. No. 4,310,440.

[51] Int. Cl.³ ............................................. B01D 15/00
[52] U.S. Cl. ................................................... 210/689
[58] Field of Search ................ 252/430, 435; 423/305; 210/689

[56] References Cited

U.S. PATENT DOCUMENTS 3,161,488 12/1964 Eastwood et al. .................. 210/689
3,441,501 4/1969 Segall et al. ........................ 210/689
3,598,546 8/1971 Good et al. ......................... 210/689

OTHER PUBLICATIONS

Bull. Soc. Chim. France, 1762 (1961), F. D'Yvoire.

*Primary Examiner*—Ivars C. Cintins
*Attorney, Agent, or Firm*—Richard G. Miller

[57] ABSTRACT

A novel family of crystalline, microporous aluminophosphate compositions is synthesized by hydrothermal crystallization at elevated temperatures of aluminophosphate gels containing a molecular structure forming template. The family comprises a number of distinct species, each with a unique crystal structure. Calcination removes volatile extraneous matter from the intracrystalline void space and yields microporous crystalline adsorbents with uniform pores, the dimensions of which vary, among the individual species, from about 3A to 10A diameter. The compositions represent a new class of adsorbents of the molecular sieve type, and also exhibit properties somewhat analogous to zeolitic molecular sieves which render them useful as catalysts or catalyst bases in chemical reactions such as hydrocarbon conversions.

2 Claims, No Drawings

ADSORPTIVE USE OF CRYSTALLINE METALLOPHOSPHATE COMPOSITIONS

RELATED APPLICATIONS

This application is a division of pending application Ser. No. 166,333 filed July 7, 1980, now U.S. Pat. No. 4,310,440.

The present invention relates in general to a novel family of crystalline compositions and to the method for their synthesis. More particularly it relates to crystalline microporous aluminophosphate compositions and to hydrothermal processes for preparing same.

Molecular sieves of the crystalline zeolite type are well known in the art and now comprise over 150 species of both naturally occurring and synthetic compositions. In general the crystalline zeolites are aluminosilicates whose frameworks are formed from $AlO_4$— and $SiO_4$ tetrahedra joined by the sharing of oxygen atoms and characterized by having pore openings of uniform dimensions, having a significant ion-exchange capacity and being capable of reversibly desorbing an adsorbed phase which is dispersed through the internal voids of the crystal without displacing any atoms which make up the permanent crystal structure.

Other crystalline microporous phases which are not zeolitic, i.e. do not contain $AlO_4$— tetrahedra as essential framework constituents, but which exhibit the ion exchange and/or adsorption characteristics of the zeolitic phases are also known. Metallorganosilicates which are said to possess ion-exchange properties, have uniform pores and are capable of reversibly adsorbing molecules having molecular diameters of about 6 A or less are reported in U.S. Pat. No. 3,941,871 issued Mar. 2, 1976 to Pwyer et al. Also a pure silica polymorph having molecular sieving properties and a neutral framework containing no cations or cation sites is defined in U.S. Pat. No. 4,061,724 issued Dec. 6, 1977 to R. W. Grose et al.

We have now discovered a new class of molecular sieve materials which are microporous three-dimensional crystalline aluminophosphate phases having uniform pore dimensions ranging from about 3 A to about 10 A and capable of making size selective separations of molecular species.

The chemistry of aluminum phosphates has been reviewed by J. H. Morris et al. (Chem. Soc. Rev., 6, 173 (1977)). The phosphates with an $Al_2O_3:P_2O_5$ molar ratio of 1:1 are the most common, and have been the most widely studied. Anhydrous $AlPO_4$ is isoelectronic and isostructural with silica and exists in quartz (as berlinite), tridymite, and cristobalite forms possessing frameworks of alternating $AlO_4$ and $PO_4$ tetrahedra. In addition to these, F. D'Yvoire [Bull. Soc. Chim. France, 1762 (1961)] has described five anhydrous crystalline $AlPO_4$ forms which have no silica analogs.

Two hydrates of $AlPO_4$ with the stoichiometry $AlPO_4.2H_2O$, metavariscite and variscite, occur in natural and synthetic forms. Their structures were determined by Kniep and coworkers (Acta Crysta., B29, 2292 (1973); ibid., B33 263 (1977), and both can be described as frameworks of alternating octahedral $AlO_4(H_2O)_2$ and tetrahedral $PO_4$ units. In both the metavariscite and variscite structures the $H_2O$ is chemically bound to the Al and, although small amounts of this water can be removed reversibly, complete dehydration is irreversible and leads to significant structural changes and the formation of anhydrous $AlPO_4$ phases.

In addition to these, six crystallographically unique, metastable hydrates have been synthesized by F. D'Yvoire (ibid.). Of these, four are reported to be reversibly dehydrated under mild conditions to yield anhydrous phases, but in each case significant changes in framework topology occurred. These changes were reported to be reversible by rehydration. It is possible therefore that the interaction between water and these aluminophosphate phases results in chemical bonding, such as the formation of $AlO_4(H_2O)_2$ octahedra, rather than physisorption.

The hydrothermal synthesis of aluminosphosphates in the presence of various alkali metal, alkaline earth, and $NH_4$ cations has been reported by Haseman and coworkers (Soil Sci. Soc. Proceed., 76 (1950); Soil Sci., 70, 257–271 (1950)), by Cole and Jackson (J. Phys. Chem.), 54, 128–142 (1950)), and by Golub and Boldog (Russ. Jour, Inorg, Chem., 21, 45 (1976)). A variety of known minerals (e.g. palmierite, taranakite, wavellite, variscite) and many novel crystalline materials were obtained. Virtually all of these materials had Al/P ratios different from 1.0. Although most of the products had appreciable $H_2O$ content only one product was examined by X-ray powder diffraction after dehydration. This product, taranakite, became amorphous at 125° C. The stability of the other phases is unknown.

R. M. Barrer and D. J. Marshall (J. Chem. Soc., 6616 (1965)) attempted to substitute P for Si during hydrothermal crystallization of mixed frameworks analogous to aluminosilicates. The crystalline products obtained from synthesis mixtures containing sources of Al, Si, and P were predominately aluminosilicates (e.g. montmorillonite, analcite, and cancrinite) and phosphates (e.g. hydroxyapatite). Several unidentified crystalline solids were observed, characterized solely by their X-ray powder diffraction patterns. Evidence for phosphorus incorporation in the aluminosilicate structures or silicon incorporation in the hydroxyapatites was not obtained, however.

G. Kuehl has used phosphate as a complexing ion for aluminum in the hydrothermal synthesis of certain zeolites (Proceedings of the London Conf. on Molecular Sieves, April 1967, p. 85; Inorg. Chem., 10, 2488 (1971)). Presumably the phosphate complexes some of the aluminum, lowering the effective concentration of the more reactive hydroxoaluminate species in the reaction mixture and, thereby, increases the ratio of silicate to hydroxoaluminate. The zeolite products had a higher Si/Al ratio than normal and presumably no incorporation of P into the zeolite frameworks was observed. In one case, a high-silica form of zeolite A contained phosphate intercalated in the sodalite cages.

In an attempt to isolate the aluminophosphate species formed when phosphate is added to a zeolite synthesis mixture, G. Kuehl prepared the crystalline compounds $[(CH_3)_4N]_3[Al(PO_4)_2] \cdot X\ H_2O$ where $X=10, 4,$ and $1.5$. They were characterized by X-ray powder diffraction, thermal, and elemental analysis, and were described as salts containing isolated $Al(PO_4)_2(OH_2)_x^{3-}$ units. Removal of all the $H_2O$ caused the decomposition of these compounds (U.S. Pat. No. 3,386,801 (1968); J. Inorg. Nucl. Chem., 31, 1943 (1969)).

The novel generic class of aluminophosphates of the present invention have an essential crystalline framework structure whose chemical composition expressed in terms of molar ratios of oxides, is $Al_2O_3:1.0\pm0.2P_2O_5;$ said framework structure being microporous in which the pores are uniform and in each species have nominal diameters within the range of from 3 to 10 Angstroms; an intra-crystalline adsorption capacity for water at 4.6 torr and 24° C. of at least 3.5 weight percent, the adsorption of water being completely reversible while retaining the same essential framework topology in both the hydrated and dehydrated state. By the term "essential framework topology" is meant the spatial arrangement of the primary Al-O and P-O bond linkages. No change in the framework topology indicates that there is no disruption of these primary bond linkages.

The present aluminophosphates are prepared by hydrothermal crystallization of a reaction mixture prepared by combining a reactive source of phosphate, alumina and water and at least one structure-directing or templating agent which can include an organic amine and a quaternary ammonium salt. In the as-synthesized form the structure-directing agent is contained within the framework structure of the aluminophosphate in amounts which vary from species to species but usually does not exceed one mole per mole of $Al_2O_3$ thereof. This structure-directing agent is readily removed by water washing or calcination and does not appear to be an essential constituent of the product aluminophosphate as evidenced by essentially complete absence of ion-exchangeability of the as-synthesized compositions and also the absence of any internally-contained organic molecules in the as-synthesized form of at least one species of the generic class. Evidence that a structure-directing agent is a critical constituent is contained in certain of the illustrative examples appearing hereinafter, wherein reaction mixtures otherwise identical to those which yield products of the present invention except for the presence of templating agents, yield instead the previously known aluminophosphate phases $AlPO_4.1.1-1.3$ $H_2O$, $AlPO_4$—tridymite, $AlPO_4$—quartz and $AlPO_4$—cristobalite.

Broadly the preparative process comprises forming a reaction mixture which in terms of molar ratios of oxides is $Al_2O_3:1\pm0.5P_2O_5:7-100H_2O$ and containing from about 0.2 to 2.0 moles of templating agent per mole of $Al_2O_3$. The reaction mixture is placed in a reaction vessel inert toward the reaction system and heated at a temperature of at least about 100° C., preferably between 100° C. and 300° C., until crystallized, usually a period from 2 hours to 2 weeks. The solid crystalline reaction product is then recovered by any convenient method, such as filtration or centrifugation, washed with water and dried at a temperature between ambient and 110° C. in air.

In a preferred crystallization method the source of phosphate is phosphoric acid, and source of alumina is a pseudo-boehmite hydrated aluminum oxide, the temperature is 125° C. to 200° C., and the crystallization time is from one to seven days. The preferred ratio of oxides in the reaction mixture is $Al_2O_3:0.8-1.2P_2O_5:25-75H_2O$ In general the most preferred reaction mixture contains per mole of $Al_2O_3$ from about 0.5-1.5 moles of templating agent, from 40-50 moles of water and about 1.0 mole of $P_2O_5$.

Not all templating agents suitably employed in the preparation of certain species of aluminophosphates of this invention are suitable for the preparation of all members of the generic class. The relationship of specific templating agents to the individual product species is apparent from the illustrative Examples set forth hereinafter.

The method of preparation and the physical and chemical properties of the various members of the present class of novel aluminophosphates are illustrated and characterized, respectively, in the following examples. The species compounds are denominated as $AlPO_4$-n wherein "n" is a number specific to each individual member.

EXAMPLE 1

Preparation of $AlPO_4$-5

A reaction mixture was prepared by combining 46.1 grams of 85% orthophsophoric acid ($H_3PO_4$) and 100.0 grams of water, to which was added 27.5 grams of a hydrated aluminum oxide (a pseudo-boehmite phase, 74.2 wt% $Al_2O_3$, 25.8 wt.% $H_2O$, a commercial product available under the trademark CATAPAL SB of the Conoco Chemicals Division of Continental Oil Company, U.S.A.) and stirred until homogeneous. To this mixture was added 176.8 grams of an aqueous solution of 23 wt.% tetrapropylammonium hydroxide (TPAOH), and the mixture stirred until homogeneous. The composition of the final reaction mixture in molar oxide ratios was:

$0.5(TPA)_2O:Al_2O_3:P_2O_5:73H_2O$

The reaction mixture was sealed in a stainless steel pressure vessel lined with polytetrafluoroethylene and heated in an oven at 150° C. at autogenous pressure for 43 hours. The solid reaction product was recovered by filtration, washed with water, and dried in air at room temperature. The major phase in the product had an X-ray powder diffraction pattern characterized by the following data wherein "I" is the intensity and "d" the interplanar spacing. The product also contained a minor amount of another crystalline impurity.

| $2\theta$ | d | $100 \times I/I_o$ |
|---|---|---|
| 7.50 | 11.8 | 100 |
| 12.95 | 6.84 | 11 |
| 14.95 | 5.93 | 28 |
| 19.75 | 4.50 | 66 |
| 20.95 | 4.24 | 63 |
| 22.4 | 3.97 | 94 |
| 24.65 | 3.61 | 5 |
| 26.00 | 3.43 | 37 |
| 28.95 | 3.08 | 21 |
| 30.05 | 2.97 | 22 |
| 33.50 | 2.67 | 5 |
| 34.50 | 2.60 | 19 |
| 36.95 | 2.43 | 5 |
| 37.50 | 2.40 | 13 |
| 40.75 | 2.21 | 1 |
| 41.60 | 2.17 | 4 |
| 42.45 | 2.13 | 4 |
| 43.65 | 2.07 | 3 |
| 44.95 | 2.02 | 2 |
| 47.70 | 1.91 | 6 |

This X-ray pattern and all other X-ray patterns appearing hereinafter were obtained using standard X-ray powder diffraction techniques. The radiation source was a high-intensity, copper target, X-ray tube operated at 50 Kv and 40 ma. The diffraction pattern from the copper Kα radiation and graphite monochromator is suitably recorded by an X-ray spectrometer scintillation counter, pulse height analyzer and strip chart recorder. Flat compressed powder samples are scanned at 2° (2 theta) per minute, using a two second time constant. Interplanar spacings (d) are obtained from the position of the diffraction peaks expressed as $2\theta$ where $\theta$ is the Bragg angle as observed on the strip chart. Intensities are determined from the heights of diffraction peaks after subtracting background.

EXAMPLE 2

Preparation of AlPO$_4$-5

(a) A reaction mixture was prepared by combining 23.1 grams of 85% orthophosphoric acid (H$_3$PO$_4$) and 44.0 grams of water, to which was added 13.7 grams of the same hydrated aluminum oxide employed in Example 1, and stirred until homogeneous. To this mixture was added 35.1 grams of an aqueous solution of 58 wt.% tetrapropylammonium hydroxide (TPAOH), and the mixture stirred until homogeneous. The composition of the final reaction mixture in molar oxide ratios was:

0.5(TPA)$_2$O:Al$_2$O$_3$:P$_2$O$_5$:40H$_2$O

The reaction mixture was sealed in a stainless steel pressure vessel lined with polytetrafluoroethylene and heated in an oven at 150° C. at autogenous pressure for 65 hours. The solid reaction product was recovered by filtration, washed with water, and dried in air at room temperature. A portion of the solids was submitted for X-ray analysis and chemical analysis.

Chemical analysis showed 7.5 wt.% C, 0.67 wt.% N, 34.2 wt.% Al$_2$O$_3$, 46.5 wt.% P$_2$O$_5$, 17.7 wt.% LOI (Loss on Ignition at 1000° C. for 4 hr) giving a product composition in molar oxide ratios of:

0.08(TPA)$_2$O:1.00Al$_2$O$_3$:0.98P$_2$O$_5$:1.3H$_2$O

The above product had an X-ray powder diffraction pattern essentially identical to that of the major phase in Example 1, and contained no crystalline impurities. This product was designated AlPO$_4$-5.

(b) A portion of the solid crystalline product obtained from a similar procedure as in part (a) above. and exhibiting an X-ray powder diffraction pattern essentially identical to that in Example 1 was calcined in air at about 500° C. for 2 hours. The calcined product had an X-ray powder diffraction pattern essentially identical to that in Example 1.

EXAMPLE 3

Preparation of AlPO$_4$-5

(a) A reaction mixture was prepared by combining 46.1 grams of 85% orthophosphoric acid (H$_3$PO$_4$) and 118.6 grams of water, to which was added 27.5 grams of a pseudo-boehmite phase (74.2 wt.% Al$_2$O$_3$, 25,8 wt.% H$_2$O), and stirred until homogeneous. To this mixture was added 29.2 grams of tripropylamine (Pr$_3$N) and the mixture stirred until homogeneous. The composition of the final reaction mixture in molar oxide ratios was:

1.0Pr$_3$N:Al$_2$O$_3$:P$_2$O$_5$:40H$_2$O

The reaction mixture was sealed in a stainless steel pressure vessel lined with polytetrafluoroethylene and heated in an oven at 150° C. at autogenous pressure for 70 hours. The solid reaction product was recovered by filtration, washed with water, and dried in air at room temperature. Chemical analysis showed 5.7 wt.% C, 0.72 wt.% N, 34.0 wt.% Al$_2$O$_3$, 48.1 wt.% P$_2$O$_5$, 16.4 wt.% LOI, giving a product composition in molar oxide ratios of:

0.16Pr$_3$N:1.00Al$_2$O$_3$:1.02P$_2$O$_5$:1.5H$_2$O

The above product had an X-ray powder diffraction pattern virtually identical to that of the major phase set forth in Example 1 and contained no crystalline impurities.

(b) A portion of the solid crystalline product obtained above was calcined in air at about 600° C. for 2 hours. The calcined product had an X-ray powder diffraction pattern essentially the same as that of the as-synthesized product of part (a) above.

EXAMPLE 4

Preparation of AlPO$_4$-5

A reaction mixture was prepared by combining 23.1 grams of 85% orthophosphoric acid (H$_3$PO$_4$) and 59.6 grams of water, to which was added 13.7 grams of a hydrated aluminum oxide, (74.2 wt.% Al$_2$O$_3$, 25.8 wt.% H$_2$O), and stirred until homogeneous. To this mixture was added 8.6 grams of tripropylamine (Pr$_3$N) and the mixture stirred until homogeneous. The composition of the final reaction mixture in molar oxide ratios was:

0.6Pr$_3$N:Al$_2$O$_3$:P$_2$O$_5$:40H$_2$O

The reaction mixture was sealed in a stainless steel pressure vessel lined with an inert plastic material and heated in an oven at 150° C. at autogenous pressure for 4 hours. The solid reaction product was recovered by filtration, washed with water, and dried in air at room temperature. The X-ray powder diffraction pattern of this product showed the crystalline AlPO$_3$-5 product of example 3 as the major phase, with a minor amount of a crystalline impurity being also present.

EXAMPLE 5

Preparation of AlPO$_4$-5

A reaction mixture was prepared by combining 46.1 grams of 85% orthophosphoric acid (H$_3$PO$_4$) and 119.2 grams of water, to which was added 27.5 grams of a hydrated aluminum oxide (74.2 wt.% Al$_2$O$_3$, 25.8 wt.% H$_2$O), and stirred until homogeneous. To this mixture was added 30.4 grams of triethylamine (Et$_3$N), and the mixture stirred until homogeneous. The composition of the final reaction mixture in molar oxide ratios was:

1.5Et$_3$N:Al$_2$O$_3$:P$_2$O$_5$:40H$_2$O

The reaction mixture was sealed in a stainless steel pressure vessel lined with polytetrafluoroethylene and heated in an oven at 200° C. at autogenous pressure for 27 hours. The solid reaction product was recovered by filtration, washed with water, and dried in air at room temperature. Chemical analysis of the product indicated the presence of 4.8 wt.% C, 0.97 wt.% N, 35.3 wt.% Al$_2$O$_3$, 49.7 wt.% P$_2$O$_5$ and 13.6 wt.% LOI, giving a product composition in molar oxide ratios of:

$$0.19 Et_3N:1.00Al_2O_3:1.01P_2O_5:1.1H_2O$$

The above product had an X-ray powder diffraction pattern essentially identical to that of the AlPO$_4$-5 product of example 1 and contained no crystalline impurities.

EXAMPLE 6

Preparation of AlPO$_4$-5

(a) A reaction mixture was prepared by combining 18.5 grams of 85% orthophosphoric acid (H$_3$PO$_4$) and 45.9 grams of water, to which was added 13.7 grams of a pseudo-boehmite phase (74.2 wt.% Al$_2$O$_3$, 25.8 wt.% H$_2$O), and stirred until homogeneous. To this mixture was added 25.9 grams of an aqueous solution of 57 wt.% tetrapropylammonium hydroxide (TPAOH), and the mixture in molar oxide ratios was:

$$0.5(TPA)_2O:Al_2O_3:0.8P_2O_5:40H_2O$$

The reaction mixture was placed in a stainless steel pressure vessel lined with an inert plastic material and heated in an oven at 150° C. at autogenous pressure for 72 hours. The solid reaction product was recovered by repeated centrifugation and washing with water, followed by filtration, washing, and drying in air at room temperature. The X-ray powder diffraction pattern of the dried product showed the major phase to be identical to AlPO$_4$-5 of example 1.

(b) A reaction mixture free of a structure-directing agent was prepared by combining 46.1 grams of 85% orthophosphoric acid (H$_3$PO$_4$) and 120 grams of water, to which was added 27.5 grams of the same hydrated aluminum oxide as in part (a) above, and stirred until homogeneous. The composition of the final reaction mixture in molar oxide ratios was:

$$Al_2O_3:P_2O_5:40H_2O$$

The reaction mixture was sealed in a stainless steel pressure vessel lined with polytetrafluoroethylene and heated in an oven at 150° C. at autogenous pressure for 72 hours. The solid reaction product was recovered by filtration, washed with water, and dried in air at 110° C. The resulting product had an X-ray powder diffraction pattern indicating a mixture of known AlPO$_4$ phases: AlPO$_4$1.1-1.3H$_2$O, and two structural analogs of crystalline silica, namely AlPO$_4$ (quartz) and AlPO$_4$ (tridymite). An identical reaction mixture heated at 200° for 24 hours produced a mixture of the same known AlPO$_4$ phases, the major products being AlPO$_4$ (quartz) and AlPO$_4$ (tridymite). No microporous AlPO$_4$ phases of the present invention were observed.

EXAMPLE 7

Preparation of AlPO$_4$-5

A reaction mixture was prepared by combining 37.8 grams of 85% orthophosphoric acid (H$_3$PO$_4$) and 177 grams of water, to which was added 67 grams of aluminum isopropoxide and stirred until homogeneous. The mixture was filtered and washed with water. To this mixture was added 145 grams of an aqueous solution of 23 wt.% tetrapropylammonium hydroxide (TPAOH), and the mixture stirred until homogeneous. The composition of the final reaction mixture in molar oxide ratios was:

$$0.5(TPA)_2O:Al_2O_3:P_2O_5:xH_2O$$

The reaction mixture was placed in a stainless steel pressure vessel lined with polytetrafluoroethylene and heated in an oven at 150° C. at autogenous pressure for 276 hours. The solid reaction product was recovered by filtration, washed with water, and dried in air at 110° C. The dried product was AlPO$_4$-5 as indicated by an X-ray powder diffraction pattern which was essentially the same as the AlPO$_4$-5 in example 1.

EXAMPLES 8–26

Preparation of AlPO$_4$-5

A procedure similar to that in example 3 was followed except where indicated in Table A below. The composition of each final mixture in molar oxide ratios was:

$$1.0R:Al_2O_3:P_2O_5:40H_2O$$

except where noted in Table A. A portion of the solid product from each reaction was examined by X-ray analysis and in each case a phase characterized by an X-ray powder diffraction pattern essentially the same as the AlPO$_4$-5 phase in example 1 was observed alone or in admixture with other products.

TABLE A

| EXAMPLE # | R | REACTION TIME (Hrs.) | REACTION TEMP., (°C.) |
|---|---|---|---|
| 8 | (C$_2$H$_5$)$_4$NOH(tetraethylammonium hydroxide) | 24 | 200 |
| 9 | N(CH$_2$CH$_2$OH) (triethanolamine) | 72 | 150 |
| 10 | piperidine | 24 | 150 |
| 11 | 2-methylpyridine | 168 | 150 |
| 12 | cyclohexylamine | 168 | 150 |
| 13 | N,N—dimethylbenzylamine | 168 | 150 |
| 14 | N,N—diethylethanolamine | 24 | 200 |
| 15 | dicyclohexylamine | 24 | 150 |
| 16 | N—N—dimethylethanolamine | 24 | 150 |
| 17 | [(CH$_3$)$_3$NCH$_2$CH$_2$OH]OH[1] | 52 | 150 |
| 18 | N,N—dimethylpiperazine[1] | 24 | 200 |
| 19 | 1,4-diazabicyclo (2,2,2) octane DABCO[2] | 192 | 200 |
| 20 | N—methyl-diethanolamine[1] | 24 | 200 |
| 21 | N—methyl-ethanolamine[1] | 24 | 200 |
| 22 | N—methylpiperidine | 24 | 200 |
| 23 | 3-methylpiperidine | 168 | 150 |
| 24 | N—methylcyclohexylamine | 24 | 200 |
| 25 | 3-methylpyridine | 24 | 150 |
| 26 | 4-methylpyridine | 168 | 150 |

[1]The final reaction mixture contains 50 H$_2$O.
[2]The final reaction mixture contains 0.5 DABCO.

The species AlPO$_4$-5 as herein referred to is a crystalline metallophosphate whose essential framework structure has a chemical composition, expressed in terms of molar ratios of oxides, is $$Al_2O_3:1.0\pm0.2P_2O_5$$

and having a characteristic X-ray powder diffraction pattern which contains at least the d-spacings set forth in Table 2, below:

TABLE 2

| 2θ | d | 100 × I/Io |
|---|---|---|
| 7.4–7.6 | 11.9–11.6 | 100 |
| 14.8–15.3 | 5.97–5.83 | 13–43 |
| 19.7–20.1 | 4.51–4.42 | 39–92 |
| 20.8–21.2 | 4.27–4.19 | 37–87 |
| 22.3–22.7 | 3.99–3.93 | 62–118 |
| 25.9–26.3 | 3.44–3.39 | 22–35 |

All of the AlPO$_4$-5 compositions for which the X-ray powder diffraction data has presently been obtained have patterns that are within the generalized pattern of Table 3, below:

TABLE 3

| 2θ | d | 100 × I/Io |
|---|---|---|
| 7.4–7.6 | 11.9–11.6 | 100 |
| 12.9–13.15 | 6.86–6.73 | 9–12 |
| 14.85–15.2 | 5.97–5.83 | 13–43 |
| 19.7–20.1 | 4.51–4.42 | 39–92 |
| 20.8–21.2 | 4.27–4.19 | 37–87 |
| 22.3–22.7 | 3.99–3.92 | 62–118 |
| 24.55–24.9 | 3.63–3.58 | 4–8 |
| 25.9–26.25 | 3.44–3.39 | 22–32 |
| 28.9–29.2 | 3.09–3.06 | 11–18 |
| 30.0–30.4 | 2.98–2.94 | 12–23 |
| 33.5–33.85 | 2.67–2.65 | 4–9 |
| 34.5–35.1 | 2.60–2.56 | 11–17 |
| 36.9–37.2 | 2.44–2.42 | 3–5 |
| 37.5–37.8 | 2.40–2.38 | 7–16 |
| 40.8–40.85 | 2.21–2.21 | 0–1 |
| 41.5–42.0 | 2.18–2.15 | 2–3 |
| 42.25–42.5 | 2.14–2.13 | 0–4 |
| 42.7–42.8 | 2.12–2.11 | 0–3 |
| 43.6–44.0 | 2.08–2.06 | 0–2 |
| 45.0–45.4 | 2.01–2.00 | 0–2 |
| 46.2 | 1.96 | 0–1 |
| 47.8 | 1.90 | 0–4 |
| 48.0–48.4 | 1.90–1.87 | 0–5 |
| 51.5–51.6 | 1.77–1.77 | 0–2 |
| 52.0 | 1.76 | 0–2 |
| 55.8–56.0 | 1.65–1.64 | 0–2 |

EXAMPLE 27

Preparation of AlPO$_4$-8

(a) A reaction mixture was prepared by combining 8.9 grams of 85% orthophosphoric acid (H$_3$PO$_4$) and 6 grams of water, to which was added 5.3 grams of a hydrated aluminum oxide (a pseudo-boehmite phase, 74.2 wt.% Al$_2$O$_3$, 25.8 wt.% H$_2$O), and 6.0 grams of water, and stirred until homogeneous. To this mixture was added 27.2 grams of an aqueous solution of 37 wt.% tetrabutylammonium hydroxide (TBAOH), and 2.0 grams of water and the mixture stirred until homogeneous. The composition of the final reaction mixture in molar oxide ratio was:

0.5(TBA)$_2$O:Al$_2$O$_3$:P$_2$O$_5$:52H$_2$O

The reaction mixture was sealed in a stainless steel pressure vessel lined with an inert plastic material and heated in an oven at 150° C. at autogenous pressure for 145 hours. The solid reaction product was recovered by filtration, washed with water, and dried in air at 115° C. Chemical analysis showed the product to contain 0.2 wt.% C, <0.05 wt.% N, 34.7 wt.% Al$_2$O$_3$, 46.6 wt.% P$_2$O$_5$, 18.4 wt.% LOI, giving a product composition in molar oxide ratios of:

1.00Al$_2$O$_3$:0.97P$_2$O$_5$:3.00H$_2$O

The major phase in the above product had an X-ray powder diffraction pattern characterized by the following data wherein "I" is the intensity and "d" the interplanar spacing; the product also contained a minor amount of a crystalline impurity.

| 2θ | d | 100 × I/I$_o$ |
|---|---|---|
| 5.3 | 16.7 | 80 |
| 6.5 | 13.6 | 100 |
| 10.0 | 8.84 | 17 |
| 10.8 | 8.19 | 2 |
| 14.6 | 6.07 | 4 |
| 16.1 | 5.56 | 16 |
| 18.8 | 4.72 | 2 |
| 19.8 | 4.48 | 8 |
| 20.2 | 4.40 | 12 |
| 21.25 | 4.19 | 82 |
| 21.9 | 4.06 | 18 |
| 22.4 | 3.97 | 39 |
| 22.7 | 3.92 | (sh)* |
| 23.55 | 3.77 | 3 |
| 24.15 | 3.68 | 11 |
| 24.9 | 3.58 | 11 |
| 27.1 | 3.29 | 2 |
| 28.2 | 3.16 | 5 |
| 31.35 | 2.853 | 4 |
| 32.9 | 2.722 | 3 |
| 34.2 | 2.622 | 1 |
| 35.6 | 2.522 | 3 |
| 38.0 | 2.368 | 9 |
| 38.4 | 2.344 | 3 (sh)* |
| 43.2 | 2.094 | 2 |
| 46.9 | 1.937 | 1 |
| 49.5 | 1.841 | 3 |

*sh = shoulder

This product was designated AlPO$_4$-8. It is to be noted that only trace amounts of the tetrabutylammonium templating compound were present in the reaction product solids. This may indicate that a templating mechanism different from that in most other species of this invention is involved.

(b) A portion of the solid crystalline product obtained above was calcined in air at about 600° C. for 2 hours. The calcined product has an X-ray powder diffraction pattern essentially the same as that of the product of part (a) above.

EXAMPLES 28–30

Preparation of AlPO$_4$-8

A procedure similar to that in example 27 was followed except where indicated in Table B. The composition of each final reaction mixture in molar oxide ratios was:

1.0R:Al$_2$O$_3$:P$_2$O$_5$:40H$_2$O where R is indicated in Table B. In each case a product phase characterized by an X-ray powder diffraction pattern essentially the same as that in example 27 was observed. Some extraneous phases were also present.

TABLE B

| EXAMPLE # | ORGANIC USED (R) | DIGESTION TIME (Hrs) | TEMP (°C.) |
|---|---|---|---|
| 28 | (n-C$_5$H$_{11}$)$_4$NOH | 24 | 150 |
| 29 | (n-C$_4$H$_9$)$_2$NH | 72 | 150 |
| 30 | (n-C$_5$H$_{11}$)$_2$NH* | 24 | 150 |

*Small amount of acetone used to wash solid product.

The species AlPO$_4$-8 as herein referred to is a crystalline metallophosphate whose essential framework structure has a chemical composition, expressed in terms of molar ratios of oxides, is Al$_2$O$_3$:1.0±0.2P$_2$O$_5$ and having a characteristic X-ray powder diffraction pattern which contains at least the d-spacings set forth in TABLE 4 below:

TABLE 4

| 2θ | d | 100 × I/Io |
|---|---|---|
| 3.3–5.4 | 16.7–16.4 | 80–100 |
| 6.5–6.65 | 13.6–13.3 | 30–100 |
| 13.7–19.8 | 4.51–4.48 | 8–29 |
| 21.2–21.3 | 4.19–4.17 | 46–82 |
| 21.8–21.9 | 4.08–4.06 | 14–56 |
| 22.4–22.9 | 3.97–3.88 | 35–39 |

All of the AlPO$_4$-8 compositions for which the X-ray powder diffraction data has presently been obtained have patterns that are within the generalized pattern of TABLE 5 below:

TABLE 5

| 2θ | d | 100 × I/Io |
|---|---|---|
| 5.3–5.4 | 16.7–17.4 | 80–100 |
| 6.5–6.65 | 13.6–13.3 | 30–100 |
| 9.9–10.1 | 8.9–8.8 | 15–20 |
| 10.75–10.8 | 8.23–8.19 | 2–9 |
| 14.6–14.8 | 6.07–5.99 | 4–17 |
| 16.1–16.2 | 5.50–5.47 | 7–16 |
| 18.8–18.9 | 4.72–4.70 | 2–12 |
| 19.7–19.8 | 4.51–4.48 | 8–29 |
| 20.1–20.2 | 4.42–4.40 | 9–12 |
| 21.2–21.3 | 4.19–4.17 | 46–82 |
| 21.8–21.9 | 4.08–4.06 | 14–56 |
| 22.4–22.5 | 3.97–3.95 } | 35–39 |
| 22.7–22.9 | 3.92–3.88 } | |
| 23.55–23.65 | 3.77–3.76 | 3–7 |
| 24.1–24.2 | 3.69–3.68 | 9–11 |
| 24.9–25.1 | 3.58–3.55 | 11–15 |
| 27.1–27.2 | 3.29–3.28 | 2–16 |
| 28.2–28.3 | 3.16–3.15 | 4–8 |
| 31.35–31.4 | 2.853–2.849 | 4–6 |
| 32.9 | 2.722 | 3–8 |
| 34.2–34.3 | 2.622–2.614 | 1–2 |
| 35.6 | 2.522 | 0–3 |
| 38.0–38.2 | 2.368–2.356 | 9–16 |
| 38.4–38.6 | 2.344–2.332 | 3–18 |
| 43.2–43.3 | 2.094–2.090 | 2–4 |
| 46.9–47.0 | 1.937–1.933 | 1–2 |
| 49.4–49.5 | 1.845–1.841 | 2–4 |

EXAMPLE 31

Preparation of AlPO$_4$-9

(a) A reaction mixture was prepared by combining 27.6 grams of 85% orthophosphoric acid (H$_3$PO$_4$) and 36.0 grams of water, to which was added 16.5 grams of a hydrated aluminum oxide (a pseudo-boehmite phase, 74.2 wt.% Al$_2$O$_3$, 25.8 wt.% H$_2$O), and stirred until homogeneous. To this mixture was added 13.5 grams of 1,4-diazabicyclo (2.2.2)octane (DABCO) dissolved in 24.0 grams of water, then 11.7 grams of water, and the mixture stirred until homogeneous. The composition of the final reaction mixture in molar oxide ratios was:

1.0DABCO:Al$_2$O$_3$:P$_2$O$_5$:40H$_2$O

The reaction mixture was sealed in a stainless steel pressure vessel lined with inert plastic and heated in an oven at 200° C. at autogenous pressure for 336 hours. The solid reaction product was recovered and washed by repeated centrifugation with water, and dried in air at 110° C. A portion of the solids was subjected to X-ray analysis and chemical analysis. Chemical analysis showed 10.6 wt.% C, 3.9 wt.% N, 32.5 wt.% Al$_2$O$_3$, 46.5 wt.% P$_2$O$_5$, 19.0 wt.% LOI, giving a product composition in molar oxide ratios of:

0.46DABCO:1.00Al$_2$O$_3$:1.03P$_2$O$_5$:0.44H$_2$O

The above product, denominated AlPO$_4$-9, had an X-ray powder diffraction pattern characterized by the following data, wherein "I" is the intensity and "d" the interplanar spacing:

| 2θ | d | 100 × I/Io |
|---|---|---|
| 8.4 | 10.3 | 12 |
| 11.1 | 7.37 | 43 |
| 12.5 | 7.00 | 18 |
| 14.0 | 6.33 | 6 |
| 15.1 | 5.87 | 5 |
| 16.8 | 5.28 | 11 |
| 18.3 | 4.85 | 29 |
| 19.3 | 4.60 | 11 |
| 21.0 | 4.23 | 100 |
| 21.9 | 4.06 | 30 |
| 22.3 | 3.99 | 18 |
| 22.8 | 3.90 | 30 |
| 25.4 | 3.51 | 38 |
| 25.7 | 3.47 | 79 |
| 26.5 | 3.36 | 13 |
| 27.7 | 3.22 | 21 |
| 28.5 | 3.13 | 29 |
| 30.6 | 2.92 | 5 |
| 31.45 | 2.843 | 10 |
| 31.8 | 2.814 | 27 |
| 32.4 | 2.763 | <1 |
| 33.15 | 2.702 | 12 |
| 33.7 | 2.660 | 18 |
| 34.3 | 2.614 | 5 |
| 34.8 | 2.578 | 3 |
| 35.5 | 2.529 | 4 |
| 36.4 | 2.468 | 1 |
| 37.8 | 2.380 | 4 |
| 38.35 | 2.347 | 10 |
| 38.45 | 2.341 | (sh)* |
| 38.9 | 2.315 | 10 |
| 41.3 | 2.186 | 2 |
| 42.15 | 2.144 | 6 |
| 42.6 | 2.122 | 4 |
| 44.55 | 2.034 } | 3 |
| 44.65 | 2.029 } | |
| 46.5 | 1.953 | 2 |
| 48.0 | 1.895 | 3 |
| 48.4 | 1.881 | 1 |
| 49.75 | 1.833 | 7 |
| 50.2 | 1.817 | 9 |
| 51.0 | 1.791 | 1 |
| 51.7 | 1.768 | (sh)* } 11 |
| 51.9 | 1.762 | 11 } |
| 53.65 | 1.708 } | 4 |
| 53.8 | 1.704 } | |
| 55.35 | 1.660 | 7 |

*sh = shoulder (b) The procedure and gel composition of part (a) above were repeated except that the reaction mixture was heated for 168 hours. AlPO$_4$-9 was produced.

The species AlPO$_4$-9 as herein referred to is a crystalline metallophosphate whose essential framework structure has a chemical composition, expressed in terms of molar ratios of oxides, is $Al_2O_3$: $1.0 \pm 0.2 P_2O_5$ and having a characteristic X-ray powder diffraction pattern which contains at least the d-spacings set forth in TABLE 6 below:

TABLE 6

| 2θ | d | 100 × I/Io |
|---|---|---|
| 11.1–11.15 | 7.97–7.94 | 43–68 |
| 12.5–12.65 | 7.08–7.00 | 12–100 |
| 18.25–18.35 | 4.86–4.83 | 19–47 |
| 21.0–21.1 | 4.23–4.21 | 41–100 |
| 25.4–25.6 | 3.51–3.48 | 38–82 |
| 25.7–25.8 | 3.47–3.45 | 0–79 |

All of the AlPO₄-9 compositions for which the X-ray powder diffraction data has presently been obtained have patterns that are within the generalized pattern of TABLE 7 below:

TABLE 7

| 2θ | d | 100 × I/Io |
|---|---|---|
| 8.4–8.5 | 10.5–10.4 | <1–22 |
| 10.8 | 8.19 | (sh) |
| 11.1–11.15 | 7.97–7.94 | 43–68 |
| 12.5–12.65 | 7.08–7.00 | 12–100 |
| 14.0–14.2 | 6.33–6.24 | 2–8 |
| 15.1–15.25 | 5.87–5.81 | 4–6 |
| 16.8–16.85 | 5.28–5.26 | 3–13 |
| 18.25–18.35 | 4.86–4.83 | 19–47 |
| 19.3–19.5 | 4.60–4.55 | 2–15 |
| 21.0–21.1 | 4.23–4.21 | 41–100 |
| 21.9–22.05 | 4.06–4.03 | 11–39 |
| 22.2–22.3 | 4.00–3.99 | (sh)–20 |
| 22.7–22.8 | 3.92–3.90 | 30–39 |
| 25.4–25.6 | 3.51–3.48 | 38–82 |
| 25.7–25.8 | 3.47–3.45 | 0–79 |
| 26.5–26.7 | 3.36–3.34 | 13–16 |
| 27.7–27.9 | 3.22–3.20 | 4–21 |
| 28.2 | 3.16 | 0–(sh) |
| 28.45–28.55 | 3.136–3.126 | 16–36 |
| 30.3–30.7 | 2.950–2.912 | 5–21 |
| 31.45–31.6 | 2.844–2.831 | (sh) |
| 31.8–31.85 | 2.814–2.810 | 14–30 |
| 33.15–33.3 | 2.702–2.691 | 5–16 |
| 33.6–33.7 | 2.667–2.660 | 12–18 |
| 34.0 | 2.637 | 0–6 |
| 34.3–34.5 | 2.614–2.600 | 5–6 |
| 34.8–34.9 | 2.578–2.571 | 0–3 |
| 35.5–35.7 | 2.529–2.515 | 4–6 |
| 36.1–36.4 | 2.488–2.468 | 1–3 |
| 37.8–38.0 | 2.380–2.368 | 2–7 |
| 38.35–38.5 | 2.347–2.338 | 4–10 |
| 38.9–39.1 | 2.315–2.304 | 8–10 |
| 41.1–41.3 | 2.196–2.186 | 0–2 |
| 42.1–42.2 | 2.146–2.141 | 3–6 |
| 42.6–42.7 | 2.122–2.118 | 2–4 |
| 44.55–44.85 | 2.034–2.021 | 1–3 |
| 46.3–46.7 | 1.961–1.945 | 2–4 |
| 48.0–48.05 | 1.895–1.893 | 3–4 |
| 48.4–48.7 | 1.881–1.870 | <1–3 |
| 49.75–50.0 | 1.833–1.824 | 0–14 |
| 50.2–50.3 | 1.817–1.814 | 0–14 |
| 51.0–51.1 | 1.791–1.787 | <1–2 |
| 51.7–51.8 | 1.768–1.765 | (sh)–12 |
| 51.9–52.1 | 1.762–1.755 | 7–11 |
| 53.65–54.0 | 1.708–1.698 | 3–4 |
| 55.3–55.5 | 1.661–1.656 | 6–8 |

EXAMPLE 32

Preparation of AlPO₄-11

(a) A reaction mixture was prepared by combining 46.0 grams of 85% orthophosphoric acid ($H_3PO_4$) and 119.2 grams of water, to which was added 27.5 grams of the same hydrated aluminum oxide as in Example 1, and stirred until homogeneous. To this mixture was added 20.3 grams of di-(n-propyl)amine($Pr_2NH$), and the mixture stirred until homogeneous. The composition of the final reaction mixture in molar oxide ratios was:

$1.0 Pr_2NH : Al_2O_3 : P_2O_5 : 40 H_2O$

The reaction mixture was sealed in a stainless steel pressure vessel lined with polytetrafluoroethylene and heated in an oven at 200° C. at autogenous pressure for 24 hours. The solid reaction product was recovered by filtration, washed with water, and dried in air at room temperature. Chemical analysis of the reaction solids showed 5.1 wt.% C., 1.00 wt.% N, 37.6 wt.% $Al_2O_3$, 51.6 wt.% $P_2O_5$, 10.4 wt.% LOI, giving a product composition in molar oxide ratios of:

$0.19 Pr_2NH : 1.00 Al_2O_3 : 0.98 P_2O_5 : 0.48 H_2O$

The above product, denominated AlPO₄-11, had an X-ray powder diffraction pattern characterized by the following data, wherein "I" is the intensity and "d" the interplanar spacing:

| 2θ | d | 100 × I/Io |
|---|---|---|
| 8.15 | 10.85 | 34 |
| 9.5 | 9.31 | 49 |
| 13.3 | 6.66 | 16 |
| 15.7 | 5.64 | 30 |
| 16.35 | 5.42 | 5 |
| 19.0 | 4.67 | 6 |
| 20.55 | 4.32 | 50 |
| 21.0 | 4.23 | 100 |
| 22.2 | 4.00 | 58 |
| 22.65 | 3.93 | 75 |
| 23.25 | 3.83 | 67 |
| 24.6 | 3.62 | 10 |
| 24.8 | 3.59 | 11 |
| 26.4 | 3.38 | 13 |
| 26.7 | 3.34 | 17 |
| 28.5 (sh)* | 3.13 | 15 |
| 28.7 | 3.11 | |
| 29.2 | 3.06 | 6 |
| 29.6 | 3.02 | 9 |
| 31.5 | 2.84 | 10 |
| 33.0 | 2.71 | 15 |
| 34.3 | 2.61 | 11 |
| 35.8 | 2.51 | 3 |
| 36.6 | 2.46 | 6 |
| 37.6 (sh)* | 2.39 | 14 |
| 37.9 | 2.37 | |
| 39.6 | 2.28 | 4 |
| 40.5 | 2.23 | 2 |
| 42.9 | 2.11 | 5 |
| 44.8 | 2.02 | 2 |
| 45.2 | 2.01 | 4 |
| 46.1 | 1.99 | 6 |
| 48.1 | 1.89 | 2 |
| 49.0 | 1.86 | 4 |
| 50.6 | 1.80 | 3 |
| 54.8 | 1.68 | 4 |

*sh = shoulder (b) A portion of a solid crystalline product exhibiting an X-ray powder diffraction pattern essentially identical to that above was calcined in air at about 200° C. for 2 hours, then at 600° C. overnight. The calcined product had an X-ray powder diffraction pattern characterized by the following data:

| 2θ | d | 100 × I/Io |
|---|---|---|
| 8.0 | 11.1 | 14 |

-continued

| 2θ | d | 100 × I/Io |
|---|---|---|
| 9.8 | 9.03 | 40 |
| 11.7 | 7.56 | 3 |
| 12.75 | 6.94 | 20 |
| 13.65 | 6.49 | 6 |
| 14.7 | 6.03 | 5 |
| 16.1 | 5.50 | 54 |
| 17.55 | 5.05 | 2 |
| 19.5 (sh) | 4.55 | 17 |
| 19.85 | 4.47 | 23 |
| 20.7 | 4.29 | 8 |
| 21.9 | 4.06 | 100 |
| 22.1 (sh) | 4.02 | 44 |
| 22.5 (sh) | 3.95 | 48 |
| 23.5 | 3.79 | 54 |
| 24.0 (sh) | 3.71 | 16 |
| 24.2 (sh) | 3.68 | 10 |
| 25.7 | 3.47 | 20 |
| 25.9 (sh) | 3.44 | 9 |
| 26.7 | 3.34 | 13 |
| 27.3 (sh) | 3.27 | 14 |
| 27.65 | 3.23 | 20 |
| 28.5 | 3.13 | 8 |
| 29.6 | 3.02 | 29 |
| 30.3 | 2.95 | 16 |
| 31.75 | 2.82 | 8 |
| 32.6 | 2.75 | 22 |
| 33.95 | 2.64 | 7 |
| 34.4 (sh) | 2.61 | 5 |
| 35.5 | 2.53 | 9 |
| 37.2 | 2.42 | 8 |
| 38.2 (sh) | 2.36 | 6 |
| 38.8 | 2.32 | 14 |
| 39.4 | 2.29 | 2 |
| 39.7 | 2.27 | 2 |
| 41.0 | 2.20 | 8 |
| 41.4 (sh) | 2.18 | 5 |
| 43.6 | 2.08 | 3 |
| 44.6 | 2.03 | 5 |
| 45.3 | 2.00 | 6 |
| 49.2 | 1.85 | 8 |
| 49.6 | 1.84 | |
| 50.4 | 1.81 | 3 |
| 52.4 | 1.75 | 1 |
| 53.6 | 1.71 | 5 |
| 54.6 | 1.68 | 2 |

(sh = shoulder)

EXAMPLES 33–36

Preparation of AlPO$_4$-11

A procedure similar to that in example 32 was followed except where indicated in Table C below. The composition of each final reaction mixture in molar oxide ratios was:

1.0R:Al$_2$O$_3$:P$_2$O$_5$:40H$_2$O

The solid product from each reaction contained in each case a phase characterized by an X-ray powder diffraction pattern essentially the same as that of the uncalcined product of example 32.

TABLE C

| EXAMPLE # | R | REACTION TIME (Hrs) | REACTION |
|---|---|---|---|
| 33 | (i-C$_3$H$_7$)$_2$NH | 24 | 200 |
| 34 | (C$_2$H$_5$) (n-C$_4$H$_9$)NH | 24 | 200 |
| 35 | (n-C$_4$H$_9$)$_2$NH | 48 | 200 |
| 36 | (n-C$_5$H$_{11}$)$_2$NH | 24 | 200 |
| 37 | (n-C$_5$H$_{11}$)$_2$NH | 24 | 150 |

The species AlPO$_4$-11 as herein referred to is a crystalline metallophosphate whose essential framework structure has a chemical composition, expressed in terms of molar ratios of oxides, is Al$_2$O$_3$:1.0±0.2P$_2$O$_5$ and having a characteristic X-ray powder diffraction pattern which contains at least the d-spacings set forth in TABLE 8 below:

TABLE 8

| 2θ | d | 100 × I/Io |
|---|---|---|
| 9.4–9.5 | 9.41–9.31 | 31–49 |
| 20.5–20.6 | 4.33–4.31 | 34–53 |
| 21.0–21.25 | 4.23–4.19 | 100 |
| 22.15–22.25 | 4.01–4.00 | 12–58 |
| 22.5–22.7 | 3.95–3.92 | 47–75 |
| 23.15–23.5 | 3.84–3.79 | 10–68 |

All of the AlPO$_4$-11 compositions for which the X-ray powder diffraction data has presently been obtained have patterns that are within the generalized pattern of TABLE 9 below:

TABLE 9

| 2θ | d | 100 × I/Io |
|---|---|---|
| 8.1–8.2 | 10.9–10.8 | 19–34 |
| 8.5–8.5 | 10.4 | (sh) |
| 9.4–9.5 | 9.41–9.31 | 49–31 |
| 13.2–13.3 | 6.71–6.66 | 11–16 |
| 15.7–15.8 | 5.64–5.61 | 16–30 |
| 16.3–16.4 | 5.44–5.40 | 3–5 |
| 19.0–19.2 | 4.67–4.62 | 4–7 |
| 20.5–20.6 | 4.33–4.31 | 34–53 |
| 21.0–21.25 | 4.23–4.19 | 100 |
| 22.15–22.25 | 4.01–4.00 | 12–58 |
| 22.5–22.7 | 3.95–3.92 | 47–75 |
| 23.15–23.5 | 3.84–3.79 | 10–68 |
| 24.6–24.8 | 3.62–3.59 | 4–10 |
| 24.8–25.0 | 3.59–3.56 | 4–11 |
| 26.3–26.4 | 3.39–3.38 | 11–18 |
| 26.6–26.8 | 3.35–3.33 | 11–18 |
| 28.3–28.5 | 3.15–3.13 | (sh) |
| 28.7–28.9 | 3.11–3.09 | 11–15 |
| 29.1–29.25 | 3.07–3.05 | 5–7 |
| 29.5–29.6 | 3.03–3.02 | 5–9 |
| 31.5–31.6 | 2.84–2.83 | 5–10 |
| 32.8–33.0 | 2.73–2.71 | 6–15 |
| 34.0–34.4 | 2.64–2.61 | 4–13 |
| 35.6–35.9 | 2.52–2.50 | 2–3 |
| 36.6–36.65 | 2.46–2.45 | 4–6 |
| 37.6 | 2.39 | 12 |
| 37.8–38.0 | 2.38–2.37 | 8–15 |
| 39.4–39.7 | 2.29–2.27 | 2–4 |
| 40.5–40.8 | 2.23–2.21 | 2 |
| 42.2–42.5 | 2.14–2.13 | 2–3 |
| 42.7–43.2 | 2.12–2.09 | 4–5 |
| 44.8–45.0 | 2.02–2.01 | 2–4 |
| 45.2–45.5 | 2.01–1.99 | 2–4 |
| 46.0–46.2 | 1.97–1.96 | 2–6 |
| 47.9–48.1 | 1.90–1.89 | 2 |
| 48.9–49.1 | 1.86–1.86 | 2–4 |
| 50.6–51.0 | 1.80–1.79 | 2–3 |
| 54.8–54.85 | 1.68–1.67 | 2–4 |
| 55.5–55.6 | 1.66–1.65 | 2 |

EXAMPLE 37

Preparation of AlPO$_4$-12

A reaction mixture was prepared by combining 46.0 grams of 85% orthophosphoric acid (H$_3$PO$_4$) and 119.2 grams of water, to which was added 27.5 grams of the same hydrated aluminum oxide as in Example 1 (a pseudoboehmite phase, 74.2 wt.% Al$_2$O$_3$, 25.8 wt.% H$_2$O), and stirred until homogeneous. To this mixture was added 6.0 grams of ethylenediamine (C$_2$H$_8$N$_2$), and the mixture stirred until homogeneous. The composition of the final reaction mixture in molar oxide ratios was:

$$0.5C_2H_8N_2:Al_2O_3:P_2O_5:40H_2O$$

The reaction mixture was sealed in a stainless steel pressure vessel lined with polytetrafluoroethylene and heated in an oven at 200° C. at autogenous pressuure for 24 hours. The solid reaction product was recovered by filtration, washed with water, and dried in air at room temperature.

Chemical analysis showed 4.3 wt.% C., 4.3 wt.% N, 35.0 wt.% $Al_2O_3$, 49.5 wt.% $P_2O_5$, 15.4 wt.% LOI, giving a product composition in molar oxide ratios of:

$$0.52C_2H_8N_2:1.00Al_2O_3:1.02P_2O_5:0.75H_2O$$

The crystalline $AlPO_4$-12 phase had an X-ray powder diffraction pattern characterized by the following data, wherein "I" is the intensity and "d" the interplanar spacing:

| 2θ | d | 100 × I/Io |
|---|---|---|
| 6.15 | 14.37 | 25 |
| 11.2 | 7.90 | 7 |
| 12.3 | 7.20 | 22 |
| 13.3 | 6.66 | 56 |
| 14.1 | 6.28 | 5 |
| 15.2 | 5.83 | 4 |
| 17.2 | 5.16 | 20 |
| 18.5 | 4.80 | 27 |
| 18.9 | 4.70 | 13 |
| 19.9 (sh) | 4.46 | — |
| 20.9 | 4.25 | 100 |
| 22.3 | 3.99 | 44 |
| 23.05 | 3.86 | 31 |
| 23.85 | 3.73 | 55 |
| 25.05 | 3.55 | 35 |
| 26.5 | 3.36 | 31 |
| 26.7 (sh) | 3.34 | |
| 27.95 (sh) | 3.19 | 20 |
| 28.2 (sh) | 3.16 | |
| 28.95 | 3.08 | 11 |
| 29.8 | 3.00 | 25 |
| 30.4 (sh) | 2.94 | 44 |
| 30.85 (sh) | 2.90 | |
| 31.15 (sh) | 2.87 | |
| 32.55 | 2.75 | 7 |
| 33.0 (sh) | 2.71 | 5 |
| 33.2 (sh) | 2.70 | |
| 34.0 | 2.64 | 18 |
| 34.8 | 2.58 | 18 |
| 37.8 | 2.38 | 4 |
| 38.6 | 2.33 | 11 |
| 39.3 | 2.29 | 9 |
| 40.0 | 2.25 | 7 |
| 40.7 | 2.22 | 9 |
| 41.8 | 2.16 | 7 |
| 42.7 (sh) | 2.12 | — |
| 43.6 | 2.08 | 5 |
| 44.5 | 2.04 | 5 |
| 45.6 | 1.99 | 4 |
| 46.6 | 1.95 | 7 |
| 48.15 | 1.89 | 9 |
| 48.6 | 1.87 | 5 |
| 50.0 | 1.82 | 5 |
| 51.8 | 1.76 | 7 |
| 52.7 | 1.74 | 4 |
| 54.6 | 1.68 | 9 |
| 55.5 | 1.66 | 2 |

(sh = shoulder)

EXAMPLE 38

Preparation of $AlPO_4$-12

A reaction mixture was prepared by combining 76.8 grams of 85% orthophosphoric acid ($H_3PO_4$) and 183.7 grams of water, to which was added 45.8 grams of the same hydrated aluminum oxide as in Example 38, and stirred until homogeneous. To this mixture was added 28.7 grams of 2-imidazolidone [$(CH_2NH)_2CO$] dissolved in 75 grams of $H_2O$, and the mixture stirred until homogeneous. The composition of the final reaction mixture in molar oxide ratios was:

$$(CH_2NH)_2CO:Al_2O_3:P_2O_5:50H_2O$$

The reaction mixture was placed in a stainless steel pressure vessel having an inert liner and heated in an oven at 200° C. at autogenous pressure for 169 hours. The solid reaction product was recovered by filtration, washed with water, and dried in air at 110° C. Chemical analysis showed 5.2 wt.% C., 6.2 wt.% N, 33.2 wt.% $Al_2O_3$, 48.2 wt.% $P_2O_5$, 18.1 wt.% LOI, giving a product composition in molar oxide ratios of:

$$0.68\ (CH_2NH)_2CO:Al_2O_3:1.04P_2O_5:0.97H_2O$$

The above product was $AlPO_4$-12 as indicated by having an X-ray powder diffraction pattern essentially identical to that in example 37.

The species $AlPO_4$-12 as herein referred to is a crystalline metallophosphate whose essential framework structure has a chemical composition, expressed in terms of molar ratios of oxides, is $$Al_2O_3: 1.0\pm0.2P_2O_5$$

and having a characteristic X-ray powder diffraction pattern which contains at least the d-spacings set forth in TABLE 10 below:

TABLE 10

| 2θ | d | 100 × I/Io |
|---|---|---|
| 6.15–6.2 | 14.37–14.26 | 25–48 |
| 13.3–13.35 | 6.66–6.63 | 56–63 |
| 20.9–21.0 | 4.25–4.44 | 100 |
| 22.3–22.4 | 3.99–3.97 | 33–45 |
| 23.85–24.0 | 3.73–3.71 | 46–61 |
| 30.85–30.95 | 2.90–2.89 | 34–44 |

All of the $AlPO_4$-12 compositions for which the X-ray powder diffraction data has presently been obtained have patterns that are within the generalized pattern of Table 11 below:

TABLE 11

| 2θ | d | I/Io × 100 |
|---|---|---|
| 6.15–6.2 | 14.37–14.26 | 48–25 |
| 11.2–11.3 | 7.90–7.83 | 15–7 |
| 12.3–12.35 | 7.20–7.17 | 34–22 |
| 13.3–13.35 | 6.66–6.63 | 63–56 |
| 14.1–14.15 | 6.28–6.26 | 8–5 |
| 15.2 | 5.83 | 4–1 |
| 17.2–17.3 | 5.16–5.13 | 29–20 |
| 18.4–18.6 | 4.82–4.77 | 37–27 |
| 18.9 | 4.70 | 16–13 |
| 19.9 | 4.46 | SH |
| 20.9–21.0 | 4.25–4.23 | 100 |
| 21.65–21.85 | 4.10–4.07 | 14–13 |
| 22.3–22.4 | 3.99–3.97 | 45–33 |
| 22.6 SH | 3.93 | 14 |
| 23.0–23.05 | 3.87–3.86 | 31–9 |
| 23.85–24.0 | 3.73–3.71 | 61–46 |

TABLE 11-continued

| 2θ | d | I/Io × 100 |
|---|---|---|
| 25.05–25.2 | 3.55–3.53 | 35–25 |
| 26.5–26.6 | 3.36–3.35 | 35–31 |
| 26.7–26.8 | 3.34–3.33 | SH |
| 27.95–28.0 | 3.19–3.19 | 6–5 |
| 28.2–28.3 | 3.16–3.15 | SH |
| 28.95–29.0 | 3.08–3.08 | 13–10 |
| 29.8–0.0 | 3.00–2.98 | 25–20 |
| 30.4 | 2.94 | SH |
| 30.85–30.95 | 2.90–2.89 | 44–34 |
| 31.1–31.2 | 2.88–2.87 | SH |
| 32.55–32.6 | 2.75–2.75 | 7–6 |
| 33.0–33.1 | 2.71–2.71 | 6–5 |
| 33.2–33.4 | 2.70–2.68 | SH |
| 34.0–34.1 | 2.64–2.63 | 18–17 |
| 34.8–34.95 | 2.58–2.57 | 19–18 |
| 35.4–35.5 | 2.54–2.53 | SH |
| 36.2 | 2.48 | 4–1 |
| 37.0 | 2.43 | 1–0 |
| 37.4 | 2.40 | 4–0 |
| 37.6–37.8 | 2.39–2.38 | 4–0 |
| 37.9 | 2.37 | SH |
| 38.3 | 2.35 | SH |
| 38.6–38.65 | 2.33–2.33 | 11–8 |
| 39.3–39.4 | 2.29–2.29 | 9–7 |
| 40.0 | 2.25 | 8–7 |
| 40.7–40.8 | 2.22–2.21 | 9–7 |
| 41.8–41.9 | 2.16–2.16 | 7–5 |
| 42.6–42.7 | 2.12–2.12 | SH |
| 43.6–43.8 | 2.08–2.07 | 7–5 |
| 44.5–44.7 | 2.04–2.03 | 5–3 |
| 45.6–45.7 | 1.99–1.99 | 4–2 |
| 46.5–46.6 | 1.95–1.95 | 7–2 |
| 48.0–48.15 | 1.90–1.89 | 9–4 |
| 48.6–48.7 | 1.87–1.87 | 5–4 |
| 50.0–50.2 | 1.82–1.82 | 8–5 |
| 51.8 | 1.76 | 8–7 |
| 52.7–5.29 | 1.74–1.73 | 4–2 |
| 54.6 | 1.68 | 9–8 |
| 55.5 | 1.66 | 2 |

EXAMPLE 39

Preparation of AlPO$_4$-14

(a) A reaction mixture was prepared by combining 57.7 grams of 85% orthophosphoric acid (H$_3$PO$_4$) and 100 grams of water, to which was added 34.4 grams of a hydrated aluminum oxide (74.2 wt.% Al$_2$O$_3$, 25.8 wt.% H$_2$O), and stirred until homogeneous. To this mixture was added 18.3 grams of t-butylamine (t-BuNH$_2$) and then 49.1 grams of water, and the mixture stirred until homogeneous. The composition of the final reaction mixture in molar oxide ratios was:

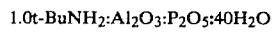

1.0t-BuNH$_2$:Al$_2$O$_3$:P$_2$O$_5$:40H$_2$O

The reaction mixture was sealed in a stainless steel pressure vessel having an inert plastic lining and heated in an oven at 150° C. at autogenous pressure for 96 hours. The solid reaction product was recovered by filtration, washed with water, and dried in air at 110° C. Chemical analysis indicated the product contained 7.2 wt.% C, 2.6 wt.% N, 34.3 wt.% Al$_2$O$_3$, 47.7 wt.% P$_2$O$_5$, 17.5 wt.% LOI, giving a product composition in molar oxide ratios of:

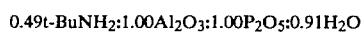

0.49t-BuNH$_2$:1.00Al$_2$O$_3$:1.00P$_2$O$_5$:0.91H$_2$O

The above product had an X-ray powder diffraction pattern characterized by the following data, wherein "I" is the intensity and "d" the interplanar spacing:

| 2θ | d | 100 × I/Io |
|---|---|---|
| 9.2 | 9.61 | 100 |
| 9.4 | 9.41 | (sh) |
| 11.2 | 7.90 | 18 |
| 13.1 | 6.76 | 17 |
| 13.4 | 6.61 | (sh) |
| 14.8 | 5.98 | 3 |
| 15.8 | 5.61 | 23 |
| 18.0 | 4.93 | 12 |
| 18.8 | 4.72 | 1 |
| 19.2 | 4.62 | 1 |
| 20.9 | 4.25 | 5 |
| 21.6 | 4.11 | 10 |
| 22.2 | 4.00 | 22 |
| 22.7 | 3.92 | 36 |
| 23.4 | 3.80 | 1 |
| 23.7 | 3.75 | 1 |
| 25.2 | 3.54 | 2 |
| 26.1 | 3.41 | 20 |
| 27.1 | 3.29 | 9 |
| 27.7 | 3.22 | 2 |
| 28.5 | 3.13 | 5 |
| 29.5 | 3.03 | 12 |
| 30.2 | 2.96 | 8 |
| 30.5 | 2.93 | (sh) |
| 30.9 | 2.89 | 4 |
| 31.2 | 2.87 | (sh) |
| 32.0 | 2.80 | 1 |
| 32.4 | 2.76 | 1 |
| 33.2 | 2.70 | (sh) |
| 33.5 | 2.67 | 6 |
| 34.1 | 2.63 | 1 |
| 35.0 | 2.56 | 1 |
| 35.5 | 2.53 | 2 |
| 36.4 | 2.47 | 3 |
| 38.1 | 2.36 | 3 |
| 38.8 | 2.32 | 5 |
| 39.5 | 2.28 | 1 |
| 40.4 | 2.23 | 5 |
| 40.8 | 2.21 | 1 |
| 42.0 | 2.15 | 2 |
| 42.4 | 2.13 | 2 |
| 43.6 | 2.08 | 1 |
| 44.0 | 2.06 | 3 |
| 44.8 | 2.02 | 3 |
| 45.9 | 1.98 | 2 |
| 46.3 | 1.96 | 2 |
| 47.8 | 1.90 | 2 |
| 48.5 | 1.88 | 2 |
| 49.8 | 1.83 | 1 |
| 51.6 | 1.77 | 2 |
| 52.7 | 1.74 | 1 |
| 53.5 | 1.71 | 4 |
| 55.7 | 1.65 | 2 |

(sh = shoulder)

The product was designated AlPO$_4$-14.

(b) A portion of the solid crystalline product obtained above was calcined in air at about 550° C. for 2 hours. The calcined product had an X-ray powder diffraction pattern characterized by the following data:

| 2θ | d | 100 × I/Io |
|---|---|---|
| 9.0 | 9.83 | 100 |
| 9.6 | 9.21 | (sh) |
| 11.5 | 7.69 | 29 |
| 12.0 | 7.38 | 9 |
| 13.2 | 6.71 | 45 |
| 13.3 | 6.66 | (sh) |
| 13.6 | 6.51 | 32 |
| 14.3 | 6.19 | 10 |
| 14.8 | 5.99 | 5 |
| 16.0 | 5.54 | 10 |
| 16.2 | 5.47 | (sh) |
| 16.8 | 5.28 | 2 |
| 18.2 | 4.87 | 35 |
| 18.6 | 4.77 | 38 |
| 18.9 | 4.70 | (sh) |

-continued

| 2θ | d | 100 × I/Io |
|---|---|---|
| 19.9 | 4.46 | 5 |
| 20.7 | 4.29 | 9 |
| 20.9 | 4.25 | 9 |
| 21.6 | 4.11 | (sh) |
| 22.0 | 4.04 | 23 |
| 22.5 | 3.95 | 29 |
| 22.8 | 3.90 | (sh) |
| 23.2 | 3.83 | 7 |
| 23.5 | 3.79 | 6 |
| 24.2 | 3.68 | 3 |
| 24.8 | 3.59 | (sh) |
| 25.1 | 3.55 | 6 |
| 25.9 | 3.44 | 3 |
| 26.6 | 3.35 | 12 |
| 27.0 | 3.30 | 20 |
| 27.4 | 3.25 | 16 |
| 27.8 | 3.21 | 11 |
| 28.0 | 3.19 | 11 |
| 28.6 | 3.12 | (sh) |
| 29.2 | 3.06 | 11 |
| 29.7 | 3.01 | 20 |
| 30.4 | 2.94 | 14 |
| 31.0 | 2.88 | 9 |
| 32.3 | 2.77 | 4 |
| 33.0 | 2.71 | 6 |
| 33.9 | 2.64 | 4 |
| 34.8 | 2.58 | 4 |
| 35.6 | 2.52 | 2 |
| 36.8 | 2.44 | 5 |
| 37.7 | 2.39 | 3 |
| 38.4 | 2.34 | 2 |
| 39.1 | 2.30 | 3 |
| 40.1 | 2.25 | 3 |
| 40.6 | 2.22 | 3 |
| 41.8 | 2.16 | 1 |
| 42.6 | 2.12 | 3 |
| 43.0 | 2.10 | 2 |
| 44.2 | 2.05 | 6 |
| 45.3 | 2.00 | 1 |
| 46.2 | 1.95 | 2 |
| 47.4 | 1.92 | 2 |
| 48.6 | 1.87 | 3 |
| 50.0 | 1.82 | 3 |
| 52.1 | 1.76 | 3 |
| 54.1 | 1.70 | 4 |

EXAMPLE 40

Preparation of AlPO$_4$-14

A reaction mixture was prepared by combining 46.1 grams of 85% orthophosphoric acid (H$_3$PO$_4$) and 119.2 grams of water, to which was added 27.5 grams of the same hydrated aluminum oxide as in Example 27 and stirred until homogeneous. To this mixture was added 11.8 grams of isopropylamine (i-PrNH$_2$), and the mixture stirred until homogeneous. The composition of the final reaction mixture in molar oxide ratios was:

1.0i-PrNH$_2$:Al$_2$O$_3$:P$_2$O$_5$:40H$_2$O

The reaction mixture was sealed in a stainless steel pressure vessel lined with an inert plastic material (polytetrafluoroethylene) and heated in an oven at 200° C. at autogenous pressure for 24 hours. The solid reaction product was recovered by filtration, washed with water, and dried in air at room temperature. Chemical analysis of the product showed 6.0 wt.% C, 2.4 wt.% N, 34.8 wt.% Al$_2$O$_3$, 48.6 wt.% P$_2$O$_5$, 16.1 wt.% LOI, giving a product composition in molar oxide ratios of:

0.49i-PrNH$_2$:1.00Al$_2$O$_3$:1.00P$_2$O$_5$:1.03H$_2$O

The above product was established to be AlPO$_4$-14 by virtue of having an X-ray powder diffraction pattern essentially identical to that of the uncalcined product in example 39.

The species AlPO$_4$-14 as herein referred to is a crystalline metallophosphate whose essential framework structure has a chemical composition, expressed in terms of molar ratios of oxides, is Al$_2$O$_3$:1.0±0.2P$_2$O$_5$ and having a characteristic X-ray powder diffraction pattern which contains at least the d-spacings set forth in Table 12 below:

TABLE 12

| 2θ | d | 100 × I/Io |
|---|---|---|
| 8.9–9.2 | 9.94–9.61 | 100–>100 |
| 11.1–11.2 | 7.97–7.90 | 18–28 |
| 13.05–13.1 | 6.78–6.76 | 17–23 |
| 15.8–15.85 | 5.61–5.59 | 21–23 |
| 22.2–22.3 | 4.00–3.99 | 22–28 |
| 22.7 | 3.92 | 36–49 |
| 26.1–26.2 | 3.44–3.40 | 20–25 |

All of the AlPO$_4$-14 compositions for which the X-ray powder diffraction data has presently been obtained have patterns that are within the generalized pattern of TABLE 12(a) below:

TABLE 12(a)

| 2θ | d | 100 × I/Io |
|---|---|---|
| 8.9–9.2 | 9.94–9.61 | 100–>100 |
| 9.4 | 9.41 | (sh) |
| 11.1–11.2 | 7.97–7.90 | 18–28 |
| 13.1 | 6.76 | 17–23 |
| 13.4 | 6.61 | (sh)–9 |
| 14.8 | 5.98 | 3 |
| 15.8–15.85 | 5.61–5.59 | 21–23 |
| 18.0 | 4.93 | 12–20 |
| 18.8 | 4.72 | 1–2 |
| 19.2 | 4.62 | 1 |
| 20.9 | 4.25 | 5–10 |
| 21.6–21.9 | 4.11–4.06 | 5–10 |
| 22.2–22.3 | 4.00–3.99 | 22–28 |
| 22.7 | 3.92 | 36–49 |
| 23.4 | 3.80 | 1 |
| 23.7–23.85 | 3.75–3.73 | 1–2 |
| 25.2–25.45 | 3.54–3.50 | 2–4 |
| 26.1–26.2 | 3.41–3.40 | 20–25 |
| 27.1–27.2 | 3.29–3.28 | 6–9 |
| 27.7 | 3.22 | 2–4 |
| 28.5–28.85 | 3.13–3.09 | (sh)–5 |
| 29.5–29.6 | 3.03–3.02 | 12–20 |
| 30.2–30.3 | 2.96–2.95 | 8–11 |
| 30.5 | 2.93 | (sh) |
| 30.9 | 2.89 | 4–18 |
| 31.2–31.3 | 2.87–2.86 | (sh) |
| 32.0–32.2 | 2.80–2.78 | 1–3 |
| 32.4–32.6 | 2.76–2.75 | 1–3 |
| 33.2–33.3 | 2.70–2.69 | (sh)–3 |
| 33.5–33.8 | 2.67–2.65 | 6–8 |
| 34.1 | 2.63 | 1 |
| 35.0–35.2 | 2.56–2.55 | 1–3 |
| 35.5–35.7 | 2.53–2.51 | 2–5 |
| 36.4–36.6 | 2.47–2.46 | 3–4 |
| 37.3 | 2.41 | 1 |
| 38.0–38.1 | 2.37–2.36 | 1–3 |
| 38.5–38.8 | 2.34–2.32 | 2–5 |
| 39.1–39.5 | 2.30–2.28 | (sh)–4 |
| 40.4–40.5 | 2.23–2.23 | 4–5 |
| 40.8–41.0 | 2.21–2.20 | 2–4 |
| 42.4 | 2.13 | 2–3 |
| 42.8 | 2.11 | 2 |
| 43.6 | 2.08 | 1 |
| 44.0–44.2 | 2.06–2.05 | 3 |
| 44.6–44.8 | 2.03–2.02 | 3 |
| 45.0 | 2.01 | 3 |
| 45.9 | 1.98 | 2 |
| 46.2–46.3 | 1.96–1.96 | 2 |

TABLE 12(a)-continued

| 2θ | d | 100 × I/Io |
|---|---|---|
| 46.6 | 1.95 | 3 |
| 47.8–48.0 | 1.90–1.90 | 2–3 |
| 48.5–48.7 | 1.88–1.87 | 2–3 |
| 49.8–50.0 | 1.83–1.82 | 1–2 |
| 51.6–52.0 | 1.77–1.76 | 2–3 |
| 52.7–52.8 | 1.73–1.74 | 1–2 |
| 53.5–54.1 | 1.71–1.70 | 4 |
| 55.2–55.7 | 1.66–1.65 | 1–2 |

(sh = shoulder)

EXAMPLE 41

Preparation of AlPO$_4$-16

(a) A reaction mixture was prepared by combining 57.7 grams of 85% orthophosphoric acid (H$_3$PO$_4$) and 69.6 grams of water, to which was added 34.4 grams of a hydrated aluminum oxide (a pseudo-boehmite phase, 74.2 wt.% Al$_2$O$_3$, 25.8 wt.% H$_2$O), and stirred until homogeneous. To this mixture was added 27.8 grams of quinuclidine (C$_7$H$_{13}$N) dissolved in 50.4 grams of water, and then 29.1 grams of water and the mixture stirred until homogeneous. The composition of the final reaction mixture in molar oxide ratios was:

1.0C$_7$H$_{13}$N:Al$_2$O$_3$:P$_2$O$_5$:40H$_2$O

The reaction mixture was sealed in a stainless steel pressure vessel lined with an inert plastic material and heated in an oven at 150° C. at autogenous pressure for 48 hours. The solid reaction product was recovered by filtration, washed with water, and dried in air at 110° C. Chemical analysis of the product indicated the presence of 7.6 wt.% C, 1.33 wt.% N, 32.4 wt.% Al$_2$O$_3$, 43.4 wt.% P$_2$O$_5$, 24.1 wt.% LOI, giving a product composition in molar oxide ratios of:

0.28C$_7$H$_{13}$N:1.00Al$_2$O$_3$:0.96P$_2$O$_5$2.45H$_2$O

The above product had an X-ray powder diffraction pattern characterized by the following data wherein "I" is the intensity and "d" the interplanar spacing:

| 2θ | d | 100 × I/Io |
|---|---|---|
| 11.3 | 7.83 | 62 |
| 15.5 | 5.72 | 2 |
| 17.3 | 5.13 | 2 |
| 18.7 | 4.75 | 50 |
| 21.9 | 4.06 | 100 |
| 22.95 | 3.875 | 9 (sh) |
| 26.55 | 3.357 | 27 |
| 27.6 | 3.23 | 2 |
| 28.0 | 3.19 | 2 |
| 29.0 | 3.08 | 12 |
| 29.75 | 3.00 | 28 |
| 32.7 | 2.739 | 4 |
| 34.7 | 2.585 | 5 |
| 37.9 | 2.374 | 8 |
| 39.6 | 2.276 | 2 |
| 44.2 | 2.049 | 2 |
| 48.5 | 1.877 | 6 |
| 52.4 | 1.746 | 3 |
| 54.8 | 1.675 | 3 |

The product was designated AlPO$_4$-16.

(b) Using the same procedure and reaction mixture composition as in part (a) except that the proportion of quinuclidine was decreased by 50 percent and the mixture was heated at 200° C. for 24 hours, AlPO$_4$-16 was again produced. A small amount of AlPO$_4$-17 was also present as an impurity.

(c) The procedure and gel composition of part (a) were followed except that the reaction mixture was heated for 16 hours. A portion of the solids was submitted for X-ray analysis. The above product was established to be AlPO$_4$-16 by virtue of having a powder diffraction pattern essentially identical with that in part (a).

(d) A portion of the solid crystalline product obtained above was calcined in air from 200° C. to 500° C. during 1 hour and then at about 500° C. for 2 hours. The calcined product had an X-ray powder diffraction pattern essentially identical to that in part (c).

The species AlPO$_4$-16 as herein referred to is a crystalline metallophosphate whose essential framework structure has a chemical composition, expressed in terms of molar ratios of oxides, is Al$_2$O$_3$:1.0±0.2P$_2$O$_5$ and having a characteristic X-ray powder diffraction pattern which contains at least the d-spacings set forth in Table 13 below:

TABLE 13

| 2θ | d | 100 × I/Io |
|---|---|---|
| 11.3–11.5 | 7.83–7.69 | 59–63 |
| 18.7–18.85 | 4.75–4.71 | 48–54 |
| 21.9–22.2 | 4.06–4.00 | 100 |
| 26.55–26.75 | 3.36–3.33 | 23–27 |
| 29.75–29.95 | 3.00–2.98 | 26–30 |

All of the AlPO$_4$-16 compositions for which the X-ray powder diffraction data has presently been obtained have patterns that are within the generalized pattern of Table 14 below:

TABLE 14

| 2θ | d | 100 × I/Io |
|---|---|---|
| 11.3–11.5 | 7.83–7.69 | 59–63 |
| 15.5–15.9 | 5.72–5.57 | 0–2 |
| 17.3–17.4 | 5.13–5.10 | 0–2 |
| 18.7–18.85 | 4.75–4.71 | 48–54 |
| 21.9–22.2 | 4.06–4.00 | 100 |
| 22.95–23.1 | 3.875–3.850 | 9–11 |
| 26.55–26.75 | 3.357–3.332 | 23–27 |
| 27.4–27.6 | 3.255–3.232 | 0–2 |
| 28.0–28.2 | 3.187–3.164 | 0–2 |
| 29.0–29.1 | 3.079–3.058 | 8–15 |
| 29.75–29.95 | 3.003–2.983 | 26–30 |
| 32.7–32.9 | 2.739–2.722 | 4–5 |
| 34.7–34.95 | 2.585–2.567 | 5–7 |
| 37.9–38.1 | 2.374–2.362 | 8–10 |
| 39.6–40.0 | 2.276–2.254 | 0–2 |
| 44.2–44.5 | 2.049–2.036 | 2–3 |
| 48.5–48.7 | 1.877–1.870 | 6–8 |
| 52.4–52.6 | 1.746–1.740 | 2–3 |
| 54.8–55.0 | 1.675–1.670 | 2–3 |

EXAMPLE 42

Preparation of AlPO$_4$-17.

(a) A reaction mixture was prepared by combining 56.7 grams of 85% orthophosphoric acid (H$_3$PO$_4$) and 69.6 grams of water, to which was added 34.4 grams of a hydrated aluminum oxide (a pseudo-boehmite phase, 74.2 wt.% Al$_2$O$_3$, 35.8 wt.% H$_2$O), and stirred until homogeneous. To this mixture was added 27.8 grams of quinuclidine (C$_7$H$_{13}$N) dissolved in 50.4 grams of water, and then 29.1 grams of water, and the mixture stirred until homogeneous. The composition of the final reaction mixture in molar oxide ratios was:

1.0C$_7$H$_{13}$N:Al$_2$O$_3$:P$_2$O$_5$:40H$_2$O

The reaction mixture was placed in a sealed stainless steel pressure vessel lined with an inert plastic material (polytetrafluoroethylene) and heated in an oven at 200° C. at autogenous pressure for 96 hours. The solid reaction product was recovered and washed by repeated centrifugation with water, and dried in air at 110° C. Chemical analysis showed 12.4 wt.% C, 2.2 wt.% N, 32.5 wt.% Al$_2$O$_3$, 45.9 wt.% P$_2$O$_5$, 21.4 wt.% LOI, giving a product composition in molar oxide ratios of:

0.46C$_7$H$_{13}$N:1.00Al$_2$O$_4$:0.99P$_2$O$_5$:0.87H$_2$O

The above product, denominated AlPO$_4$-17 had an X-ray powder diffraction pattern characterized by the following data, wherein "I" is the intensity and "d" the interplanar spacing:

| 2θ | d | 100 × I/Io |
|---|---|---|
| 7.65 | 11.55 | 100 |
| 9.7 | 9.12 | 41 |
| 11.35 | 7.79 | 2 |
| 11.9 | 7.44 | 3 |
| 13.35 | 6.63 | 39 |
| 14.2 | 6.24 | 13 |
| 14.7 | 6.03 | 2 |
| 15.4 | 5.75 | 62 |
| 16.6 | 5.34 | 33 |
| 18.0 | 4.93 | 20 |
| 18.8 | 4.72 | 2 |
| 19.6 | 4.53 | 67 |
| 20.5 | 4.33 | 93 |
| 21.4 | 4.15 | 50 |
| 22.1 | 4.02 | 2 |
| 22.5 | 3.95 | 15 |
| 23.3 | 3.82 | 34 |
| 23.8 | 3.74 | 39 |
| 24.2 | 3.68 | 3 |
| 25.3 | 3.52 | 55 |
| 26.95 | 3.38 | 35 |
| 27.4 | 3.26 | 20 |
| 28.05 | 3.18 | 5 |
| 28.7 | 3.11 | 20 |
| 30.6 | 2.92 | 17 |
| 31.2 | 2.87 | 29 |
| 31.8 | 2.81 | 68 |
| 32.4 | 2.76 | 2 |
| 33.5 | 2.67 | 18 |
| 34.0 | 2.64 | 2 |
| 34.6 | 2.59 | 2 |
| 35.15 | 2.55 | 2 |
| 35.9 | 2.50 | 7 |
| 36.4 | 2.47 | 6 |
| 36.8 | 2.44 | 2 |
| 37.3 | 2.41 | 2 |
| 38.0 | 2.37 | 3 |
| 39.4 | 2.29 | 2 |
| 39.8 | 2.26 | 7 |
| 40.4 | 2.23 | 4 |
| 41.2 | 2.19 | 3 |
| 42.2 | 2.14 | 3 |
| 42.8 | 2.11 | 1 |
| 43.6 | 2.08 | 9 |
| 44.45 | 2.04 | 2 |
| 45.75 | 1.98 | 5 |
| 46.2 | 1.96 | 1 |
| 46.6 | 1.95 | 4 |
| 47.8 | 1.90 | 3 |
| 48.6 | 1.87 | 2 |
| 49.25 | 1.85 | 8 |
| 49.65 | 1.84 | 11 |
| 50.2 | 1.82 | 2 |
| 51.25 | 1.78 | 1 |
| 52.0 | 1.76 | 11 |

-continued

| 2θ | d | 100 × I/Io |
|---|---|---|
| 53.2 | 1.72 | 1 |
| 53.85 | 1.70 | 5 |
| 55.45 | 1.66 | 8 |

(b) A portion of the solid crystalline product obtained after continuing the digestion of the above reaction mixture to 168 hours exhibited an X-ray powder diffraction pattern essentially identical to that above.

(c) A portion of the product from part (b) calcined in air at about 550° C. for 2 hours. The calcined product had an X-ray powder diffraction pattern characterized by the following data:

| 2θ (°) | d (A) | 100 × I/Io |
|---|---|---|
| 7.7 | 11.5 | 77 |
| 9.7 | 9.1 | 46 |
| 11.6 | 7.63 | 13 |
| 11.85 | 7.47 | |
| 13.45 | 6.58 | 100 |
| 14.0 | 6.33 | 21 |
| 14.2 | 6.24 | 28 |
| 14.8 | 5.99 | 2 |
| 15.6 | 5.68 | 16 |
| 16.8 | 5.28 | 6 |
| 18.0 | 5.22 | 3 |
| 19.2 | 4.62 | 5 |
| 19.65 | 4.52 | 12 |
| 20.5 | 4.33 | 42 |
| 20.8 | 4.27 | |
| 21.6 | 4.11 | 22 |
| 22.2 | 4.00 | 2 |
| 22.6 | 3.93 | 2 |
| 23.65 | 3.76 | 29 |
| 23.95 | 3.72 | |

| 2θ | d | 100 × I/Io |
|---|---|---|
| 24.4 | 3.65 | 22 |
| 24.6 | 3.63 | |
| 25.0 | 3.56 | 7 |
| 25.3 | 3.52 | 12 |
| 26.2 | 3.40 | 7 |
| 27.3 | 3.26 | 20 |
| 28.2 | 3.16 | 15 |
| 28.8 | 3.10 | 10 |
| 29.4 | 3.038 | 7 |
| 29.6 | 3.018 | |
| 30.1 | 2.969 | 7 |
| 30.8 | 2.903 | 7 |
| 31.4 | 2.849 | 24 |
| 31.9 | 2.805 | 15 |
| 32.1 | 2.788 | |
| 33.7 | 2.660 | 11 |
| 35.2 | 2.550 | 1 |
| 36.1 | 2.488 | 7 |
| 36.35 | 2.471 | |
| 39.6 | 2.281 | 2 |
| 41.3 | 2.186 | 3 |
| 42.0 | 2.151 | 2 |
| 42.7 | 2.118 | 4 |
| 43.8 | 2.067 | 1 |
| 44.9 | 2.019 | 1 |
| 46.1 | 1.973 | 1 |
| 46.6 | 1.953 | 2 |
| 47.4 | 1.972 | 3 |
| 48.0 | 1.895 | 2 |
| 49.2 | 1.852 | 2 |
| 50.2 | 1.817 | 7 |
| 51.3 | 1.781 | 7 |
| 52.8 | 1.734 | 2 |

| | | |
|---|---|---|
| 54.0 | 1.698 | 1 |
| 55.3 | 1.661 | 2 |

EXAMPLE 43

Preparation of AlPO$_4$-17

A reaction mixture was prepared by combining 115.3 grams of 85% orthophosphoric acid (H$_3$PO$_4$) and 256 grams of water, to which was added 68.7 grams of a hydrated aluminum oxide (a pseudo-boehmite phase, 74.2 wt.% Al$_2$O$_3$, 25,8 wt.% H$_2$O), and stirred until homogeneous. To this mixture was added 43.6 grams of neopentylamine (C$_5$H$_{13}$N) and then 44.1 grams of water, and the mixture sitrred until homogeneous. The composition of the final reaction mixture in molar oxide ratios was:

$$1.0C_5H_{13}N:Al_2O_3:P_2O_5:40H_2O$$

The reaction mixture was placed in a stainless steel pressure vessel lined with an inert plastic material (polytetrafluoroethylene) and heated in an oven at 150° C. at autogenous pressure for 168 hours. The solid reaction product was recovered and washed by repeated centrifugation with water, and dried in air at 110° C. Chemical analysis showed 9.9 wt.% C, 2.5 wt.% N, 32.6 wt.% Al$_2$O$_3$, 44.2 wt.% P$_2$O$_5$, 21.8 wt.% LOI, giving a product composition in molar oxide ratios of:

$$0.52C_5H_{13}N:1.00Al_2O_3:0.97P_2O_5:1.28H_2O$$

The major phase in the above product had an X-ray powder diffraction pattern very similar to that of the product in example 42 (a). The product was designated AlPO$_4$-17.

EXAMPLES 44-45

Preparation of AlPO$_4$-17.

A procedure similar to that in example 42 was followed except where indicated in Table D. The composition of each final reaction mixture in molaroxide ratios was:

$$1.0R:Al_2O_3:P_2O_5:40H_2O$$

where R is indicated in Table D. A portion of the solid product from each reaction was subjected to X-ray analysis and in each case a phase characterised by an X-ray powder diffraction pattern essentially the same as that of the product of example 42 (a) was observed.

TABLE D

| EXAMPLE # | R | REACTION TIME (Hrs) | REACTION TEMP. (°C.) |
|---|---|---|---|
| 44 | Cyclohexylamine | 168 | 200 |
| 45 | Piperidine | 168 | 200 |

The species AlPO$_4$-17 as herein referred to is a crystalline metallophosphate whose essential framework structure has a chemical composition, expressed in terms of molar ratios of oxides, is $$Al_2O_3:1.0\pm0.2P_2O_5$$

and having a characteristic X-ray powder diffraction pattern which contains at least the d-spacings set forth in Table 15 below:

TABLE 15

| 2θ | d | 100 × I/Io |
|---|---|---|
| 7.6-7.8 | 11.6-11.33 | 100 |
| 13.25-13.5 | 6.68-6.56 | 39-54 |
| 15.35-15.6 | 5.77-5.68 | 26-62 |
| 19.55-19.75 | 4.54-4.50 | 14-67 |
| 20.35-20.65 | 4.36-4.30 | 45-93 |
| 21.25-21.5 | 4.18-4.13 | 20-50 |
| 25.3-25.45 | 3.52-3.50 | 12-55 |
| 31.65-31.85 | 2.83-2.81 | 19-68 |

All of the AlPO$_4$-17 compositions for which the X-ray powder diffraction data has presently been obtained have patterns that are within the generalized pattern of Table 16 below:

TABLE 16

| 2θ | d | 100 × I/Io |
|---|---|---|
| 7.6-7.8 | 11.6-11.33 | 100 |
| 9.7-9.9 | 9.12-8.93 | 15-41 |
| 11.35-11.9 | 7.80-7.44 | 4-5 |
| 13.25-13.5 | 6.68-6.56 | 39-54 |
| 14.2-14.4 | 6.24-6.15 | 2-13 |
| 15.35-15.6 | 5.77-5.68 | 26-62 |
| 16.5-16.7 | 5.37-5.31 | 10-33 |
| 17.9-18.15 | 4.96-4.89 | 4-20 |
| 19.55-19.75 | 4.54-4.50 | 14-67 |
| 20.35-20.65 | 4.36-4.30 | 45-93 |
| 21.25-21.5 | 4.18-4.13 | 20-50 |
| 21.7-21.8 | 4.10-4.08 | (sh) |
| 22.5-22.65 | 3.95-3.93 | 3-15 |
| 23.1-23.45 | 3.85-3.79 | 17-34 |
| 23.7-23.95 | 3.75-3.72 | 14-39 |
| 24.1-24.2 | 3.69-3.68 | (sh) |
| 25.3-25.45 | 3.52-3.50 | 12-55 |
| 26.75-27.0 | 3.33-3.30 | 14-35 |
| 27.35-27.5 | 3.26-3.24 | 5-20 |
| 27.85-28.2 | 3.20-3.16 | 2-5 |
| 28.6-28.8 | 3.12-3.10 | 5-20 |
| 29.45-29.8 | 3.03-3.00 | 2-1 |
| 30.45-30.7 | 2.94-2.91 | 4-17 |
| 31.0-31.3 | 2.88-2.86 | 13-29 |
| 31.65-31.85 | 2.83-2.81 | 19-68 |
| 32.3-32.4 | 2.77-2.76 | 1-2 |
| 33.4-33.6 | 2.68-2.67 | 18-8 |
| 34.0 | 2.64 | 2 |
| 34.6 | 2.59 | 2 |
| 35.15 | 2.55 | 2 |
| 35.7-36.0 | 2.51-2.49 | 4-7 |
| 36.3-36.6 | 2.47-2.45 | 1-6 |
| 36.8 | 2.44 | 2 |
| 37.3 | 2.41 | 2 |
| 37.8-38.0 | 2.38 | 1-3 |
| 39.2-39.4 | 2.30 | 2 |
| 39.65-39.9 | 2.27-2.26 | 2-7 |
| 40.3-40.5 | 2.24-2.23 | 1-4 |
| 41.0-41.2 | 2.20-2.19 | 1-3 |
| 41.9-42.2 | 2.16-2.14 | 1-3 |
| 42.8 | 2.11 | 1 |
| 43.6-43.8 | 2.08-2.07 | 2-9 |
| 44.45 | 2.04 | 2 |
| 45.5-45.8 | 1.99-1.98 | 1-5 |
| 46.2 | 1.97 | 1 |
| 46.5-46.7 | 1.95-1.95 | 1-4 |
| 47.35-47.8 | 1.92-1.90 | 1-3 |
| 48.55-48.8 | 1.88-1.87 | 1-2 |
| 49.25 | 1.85 | 8 |
| 49.45-49.7 | 1.84-1.83 | 4-11 |
| 50.2-5025 | 1.82-1.82 | 1-2 |
| 51.25 | 1.78 | 1 |
| 52.0-52.2 | 1.76-1.75 | 3-11 |
| 53.1-53.2 | 1.72-1.72 | 1 |
| 53.75-54.0 | 1.71-1.70 | 1-5 |
| 55.2-55.5 | 1.66-1.66 | 3-8 |

(sh = shoulder)

EXAMPLE 46

Preparation of AlPO$_4$-18.

A reaction mixture was prepared by combining 46.1 grams of 85% orthophosphoric acid (H$_3$PO$_4$) and 53.8 grams of water, to which was added 27.5 grams of a pseudo-boehmite phase, (74.2 wt.% Al$_2$O$_3$, 25.8 wt.% H$_2$O), and stirred until homogeneous. To this mixture was added an aqueous solution prepared by combining 6.5 grams of 37 wt.% HCl and 98.0 grams of 40 wt.% tetraethylammonium hydroxide (TEAOH), and the mixture stirred until homogeneous. The composition of the final reaction mixture in molar oxide ratios was:

0.33HCl:0.67(TEA)$_2$O:Al$_2$O$_3$:P$_2$O$_5$:40H$_2$O

The reaction mixture was placed in a sealed stainless steel pressure vessel lined with an inert plastic material (polytetrafluoroethylene) and heated in an oven at 150° C. at autogenous pressure for 336 hours. The solid reaction product was recovered by filtration, washed with water, and dried in air at room temperature. Chemical analysis showed 8.9 wt.% C, 1.28 wt.% N, 33.5 wt.% Al$_2$O$_3$, 38.9 wt.% P$_2$O$_5$, 26.4 wt.% LOI, giving a product composition in molar oxide ratios of:

0.14(TEA)$_2$O:1.00Al$_2$O$_3$:0.83P$_2$O$_5$:0.9H$_2$O

The above product contained a minor amount of crystalline impurity but the major phase, denominated AlPO$_4$-18, had an X-ray powder diffraction pattern characterized by the following data, wherein "I" is the intensity and "d" the interplanar spacing:

| 2θ | d | 100 × I/Io |
|---|---|---|
| 9.60 | 9.21 | 100 |
| 10.45 | 8.47 | 8 |
| 11.0 | 8.04 | 9 |
| 13.1 | 6.76 | 6 |
| 14.0 | 6.33 | 8 |
| 14.8 | 5.99 | 10 |
| 15.5 | 5.72 | 27 |
| 16.9 | 5.25 | |
| 17.0 | 5.22 | 61 |
| 17.9 | 4.96 | 20 |
| 19.3 | 4.60 | |
| 19.5 | 4.55 | 17 |
| 20.15 | 4.41 | 35 |
| 20.95 | 4.24 | 45 |
| 22.1 | 4.02 | |
| 22.3 | 3.99 | 17 |
| 23.3 | 3.82 | 5 |
| 23.85 | 3.73 | 6 |
| 24.4 | 3.65 | 14 |
| 24.9 | 3.58 | 9 |
| 25.4 | 3.51 | 6 |
| 26.1 | 3.41 | 13 |
| 26.45 | 3.37 | |
| 26.8 | 3.33 | 12 |
| 28.0 | 3.19 | 16 |
| 29.0 | 3.08 | 7 |
| 30.0 | 2.98 | 20 |
| 30.75 | 2.91 | 14 |
| 31.3 | 2.86 | 14 |
| 31.8 | 2.81 | |
| 32.4 | 2.76 | 24 |
| 33.4 | 2.68 | 6 |
| 34.5 | 2.60 | 3 |
| 35.8 | 2.51 | |
| 36.2 | 2.48 | 3 |
| 38.2 | 2.36 | 2 |
| 40.2 | 2.24 | 1 |
| 41.7 | 2.17 | 3 |
| 42.9 | 2.11 | 5 |
| 47.8 | 1.90 | 3 |
| 48.6 | 1.87 | 2 |
| 49.6 | 1.84 | 4 |
| 51.0 | 1.79 | 4 |
| 52.0 | 1.76 | 2 |
| 54.2 | 1.69 | 4 |
| 55.1 | 1.67 | 2 |

The species AlPO$_4$-18 as herein referred to is a crystalline metallophosphate whose essential framework structure has a chemical composition, expressed in terms of molar ratios of oxides, is Al$_2$O$_3$:1.0±0.2P$_2$O$_5$ and having a characteristic X-ray powder diffraction pattern which contains at least the d-spacings set forth in Table 17 below:

TABLE 17

| 2θ | d | 100 × I/Io |
|---|---|---|
| 9.60–9.65 | 9.21–9. | 100 |
| 15.5–15.55 | 5.72–5.70 | 27–34 |
| 16.9–17.1 | 5.25–5.19 | 61–70 |
| 17.9 | 4.96 | 20–25 |
| 20.15–20.25 | 4.41–4.39 | 35–43 |
| 20.95–21.05 | 4.24–4.22 | 45–52 |
| 30.0–30.1 | 2.98–2.97 | 20–25 |
| 31.8–32.5 | 2.81–2.75 | 24–27 |

All of the AlPO$_4$-18 compositions for which the X-ray powder diffraction data has presently been obtained have patterns that are within the generalized pattern of Table 18 below:

TABLE 18

| 2θ | d | 100 × I/Io |
|---|---|---|
| 9.60–9.65 | 9.21–9.17 | 100 |
| 10.45–10.50 | 8.47–8.42 | 8 |
| 11.0–11.05 | 8.04–8.01 | 9–12 |
| 13.1–13.2 | 6.76–6.71 | 6–7 |
| 14.0 | 6.33 | 8 |
| 14.8–14.85 | 5.99–5.97 | 10–11 |
| 15.5–15.55 | 5.72–5.70 | 27–34 |
| 16.9–17.1 | 5.25–5.19 | 61–70 |
| 17.9 | 4.96 | 20–25 |
| 19.35–19.6 | 4.59–4.53 | 8–17 |
| 20.15–20.25 | 4.41–4.39 | 35–43 |
| 20.95–21.05 | 4.27–4.22 | 45–52 |
| 22.1–22.3 | 4.02–3.99 | 17–19 |
| 23.3–23.4 | 3.82–3.80 | 5–7 |
| 23.85–24.0 | 3.73–3.71 | 6–8 |
| 24.4–24.5 | 3.65–3.63 | 14 |
| 24.9–25.0 | 3.58–3.56 | 9–11 |
| 25.4–25.55 | 3.51–3.49 | 6–7 |
| 26.1–26.2 | 3.41–3.40 | 13–15 |
| 26.45–26.9 | 3.37–3.31 | 12 |
| 28.0–28.2 | 3.19–3.16 | 16–17 |
| 30.0–30.1 | 3.98–3.97 | 20–25 |
| 30.75–30.9 | 2.91–2.87 | 14–17 |
| 31.3–31.4 | 2.86–2.85 | 14–15 |
| 31.8–32.5 | 2.81–2.75 | 24–27 |
| 33.3–33.55 | 2.69–2.67 | 6 |
| 34.5–34.6 | 2.60–2.59 | 3–4 |
| 35.8–36.2 | 2.51–2.48 | 3–4 |
| 40.0–40.2 | 2.25–2.24 | 1–2 |
| 41.7–41.8 | 2.17–2.16 | 2–3 |
| 42.9–43.0 | 2.11–2.10 | 5 |

TABLE 18-continued

| 2θ | d | 100 × I/Io |
|---|---|---|
| 47.8 | 1.90 | 3–4 |
| 49.6 | 1.84 | 4–5 |
| 51.0 | 1.79 | 4–7 |
| 52.0 | 1.76 | 2–4 |
| 54.2–54.4 | 1.69–1.69 | 3–4 |

(b) A portion of the solid crystalline product obtained from a similar preparation and exhibiting an X-ray powder diffraction pattern essentially identical to that of part (a) was calcined stepwise in 100° increments from 100° to 600° C., being held at each temperature for one hour before the next increment. The calcined product had an X-ray powder diffraction pattern characterized by the following data:

| 2θ | d | 100 × I/Io |
|---|---|---|
| 9.5 | 9.31 | 100 |
| 10.0 | 8.85 | sh |
| 10.4 | 8.51 | sh |
| 10.6 | 8.35 | 14 |
| 11.3 | 7.83 | 4 |
| 12.95 | 6.83 | 9 |
| 13.5 | 6.56 | 8 |
| 14.5 | 6.11 | 4 |
| 16.1 | 5.50 | 11 |
| 17.0 | 5.22 | 18 |
| 17.2 | 5.16 | 17 |
| 19.1 | 4.65 | 5 |
| 19.7 | 4.51 | 7 |
| 20.0 | 4.44 | 6 |
| 20.7 | 4.29 | 12 |
| 21.3 | 4.17 | 15 |
| 21.9 | 4.06 | 5 |
| 22.5 | 3.95 | 8 |
| 22.9 | 3.88 | 9 |
| 23.9 | 3.72 | 12 |
| 24.3 | 3.66 | sh |
| 24.9 | 3.58 | 3 |
| 25.2 | 3.53 | 3 |
| 25.7 | 3.47 | sh |
| 26.0 | 3.43 | 8 |
| 26.3 | 3.39 | 7 |
| 27.1 | 3.29 | 4 |
| 27.8 | 3.21 | 7 |
| 29.1 | 3.07 | 7 |
| 30.0 | 2.98 | 8 |
| 30.4 | 2.94 | sh |
| 31.0 | 2.88 | 13 |
| 31.6 | 2.83 | 5 |
| 32.2 | 2.78 | 7 |
| 32.6 | 2.75 | sh |
| 33.0 | 2.71 | sh |
| 33.7 | 2.66 | 4 |
| 34.7 | 2.59 | 3 |
| 37.0 | 2.43 | 2 |
| 38.8 | 2.32 | 2 |
| 43.2 | 2.09 | 2 |
| 49.0 | 1.86 | 4 |
| 55.2 | 1.66 | 3 |
| 55.8 | 1.65 | 2 |

EXAMPLE 47.

Preparation of AlPO$_4$-20.

(a) A reaction mixture was prepared by combining 23.1 grams of 85% orthophosphoric acid (H$_2$PO$_4$) and 34.6 grams of water, to which was added 13.8 grams of a hydrated aluminum oxide (a pseudo-boehmite phase, 74.2 wt.% Al$_2$O$_3$, 25.8 wt.% H$_2$O), and stirred until homogeneous. To this mixture was added 36.2 grams of tetramethylammonium hydroxide pentahydrate (TMAOH.5H$_2$O) dissolved in 50 grams of H$_2$O and the mixture stirred until homogeneous. The composition of the final reaction mixture in molar oxide ratios was:

0.5(TMA)$_2$O:Al$_2$O$_3$:P$_2$O$_5$:43 H$_2$O

The reaction mixture was sealed in a stainless steel pressure vessel lined with polytetrafluoroethylene and heated in an oven at 150° C. at autogenous pressure for 71 hours. The solid reaction product was recovered by repeated centrifugation and washing with water, and dried in air at room temperature. Chemical analysis of the product showed 6.0 wt.% C, 1.76 wt.% N, 32.7 wt.% Al$_2$O$_3$, 44.8 wt.% P$_2$O$_5$, 22.8 wt.% LOI, giving a product composition in molar oxide ratios of:

0.20(TMA)$_2$O:1.00Al$_2$O$_3$:0.98P$_2$O$_5$:2.17H$_2$O

The AlPO$_4$-20 product contained a minor amount of crystalline impurity, but the major phase had an X-ray powder diffraction pattern characterized by the following data, wherein "I" is the intensity and "d" the interplanar spacing:

| 2θ | d | 100 × I/Io |
|---|---|---|
| 14.0 | 6.326 | 51 |
| 19.9 | 4.462 | 44 |
| 22.3 | 3.986 | 16 |
| 24.5 | 3.633 | 100 |
| 28.2 | 3.164 | 25 |
| 31.6 | 2.831 | 18 |
| 34.7 | 2.585 | 18 |
| 40.3 | 2.238 | 4 |
| 43.1 | 2.099 | 5 |
| 47.8 | 1.903 | 4 |
| 52.2 | 1.752 | 10 |

(b) A portion of the solid crystalline product obtained from a similar preparation and exhibiting an X-ray powder diffraction pattern essentially identical to that of part (a) was calcined in air at about 100° C. for 1 hour, 200° C. for 1 hour, 400° C. for 1 hour and finally at 620° C. for 1 hour. The calcined product had an X-ray powder diffraction pattern characterized by the following data:

| 2θ | d | 100 × I/Io |
|---|---|---|
| 14.3 | 6.19 | 100 |
| 20.3 | 4.37 | 27 |
| 22.7 | 3.92 | 9 |
| 24.8 | 3.59 | 57 |
| 28.4 | 3.14 | 20 |
| 32.1 | 2.79 | 19 |
| 35.1 | 2.56 | 13 |
| 40.9 | 2.21 | 4 |
| 52.7 | 1.74 | 6 |

AlPO$_4$-20 appears to be a structural analogue of the aluminosilicate sodalite.

EXAMPLE 48.

Preparation of AlPO$_4$-20.

A reaction mixture was prepared by combining 57.6 grams of 85% orthophosphoric acid (H$_3$PO$_4$) and 90.5 grams of water, to which was added 37.8 grams of the same hydrated aluminum oxide as in Example 47 and stirred until homogeneous. To this mixture was added 36.2 grams of tetramethylammonium hydroxide pentahydrate (TMAOH.5H$_2$O) and 2.0 grams of sodium hydroxide dissolved in 50 grams of H$_2$O, and the mixture stirred until homogeneous. The composition of the final reaction mixture in molar oxide ratios was:

0.1Na$_2$O:0.4(TMA)$_2$O:1.1Al$_2$O$_3$:P$_2$O$_5$:43H$_2$O

The reaction mixture was placed in a sealed stainless steel pressure vessel lined with an inert plastic material and heated in an oven at 150° C. at autogenous pressure for 72 hours. The solid reaction product was recovered by centrifuging and washing with water, and dried in air at 110° C. A portion of the solids was subjected to X-ray analysis. The AlPO$_4$-20 product had an X-ray powder diffraction pattern essentially identical to that of the uncalcined product in example 47 (a).

EXAMPLE 49.

Preparation of AlPO$_4$-20.

A reaction mixture was prepared by combining 92.1 grams of 85% orthophosphoric acid (H$_3$PO$_4$) and 220.9 grams of water, to which was added 55.0 grams of a hydrated aluminum oxide (Catapal SB, a pseudo-boehmite phase, 74.2 wt.% Al$_2$O$_3$, 25.8 wt.% H$_2$O), and stirred until homogeneous. To this mixture was added 72.5 grams of tetramethylammonium hydroxide pentahydrate (TMAOH.5H$_2$O) dissolved in 50 grams H$_2$O and the mixture stirred until homogeneous. To this mixture 13.0 grams of NaA zeolite were added and the mixture homogenized. Exclusive of the NaA zeolite, the composition of the final reaction mixture in molar oxide ratios was:

0.5(TMA)$_2$O:Al$_2$O$_3$:P$_2$O$_5$:50H$_2$O

The reaction mixture was placed in a stainless steel pressure vessel having an inert plastic lining and heated in an oven at 125° C. at autogenous pressure for 53 hours. The solid reaction product was recovered by centrifuging and washing with water, and dried in air at 110° C. The AlPO$_4$-20 product had an X-ray powder diffraction pattern essentially identical to that of the product in Example 47 (a).

The species AlPO$_4$-20 as herein referred to is a crystalline metallophosphate whose essential framework structure has a chemical composition, expressed in terms of molar ratios of oxides, is Al$_2$O$_3$:1.0±0.2P$_2$O$_5$ and having a characteristic X-ray powder diffraction pattern which contains at least the d-spacings set forth in Table 19 below:

TABLE 19

| 2θ | d | 100 × I/Io |
|---|---|---|
| 13.9–14.1 | 6.37–6.28 | 40–55 |
| 19.8–20.0 | 4.48–4.44 | 40–48 |
| 24.3–24.5 | 3.66–3.63 | 100 |
| 28.2–28.3 | 3.16–3.15 | 12–25 |
| 31.4–31.7 | 2.85–2.82 | 11–18 |
| 34.6–34.8 | 2.59–2.58 | 15–18 |

All of the AlPO$_4$-20 compositions for which the X-ray powder diffraction data has presently been obtained have patterns that are within the generalized pattern of Table 20 below:

TABLE 20

| 2θ | d | 100 × I/Io |
|---|---|---|
| 13.9–14.1 | 6.37–6.28 | 40–55 |
| 19.8–20.0 | 4.48–4.44 | 40–48 |
| 22.2–22.4 | 4.00–3.97 | 5–16 |
| 24.3–24.5 | 3.66–3.63 | 100 |
| 28.2–28.3 | 3.16–3.15 | 12–25 |
| 31.4–31.7 | 2.85–2.82 | 11–18 |
| 34.6–34.8 | 2.59–2.58 | 15–18 |
| 40.2–40.5 | 2.24–2.23 | 4–5 |
| 42.7–43.1 | 2.12–2.01 | 5–8 |
| 47.5–47.8 | 1.91–1.90 | 4–7 |
| 51.9–52.2 | 1.76–1.75 | 10–11 |

EXAMPLE 50.

Preparation of AlPO$_4$-22.

(a) A reaction mixture was prepared by combining 57.7 grams of 85% orthophosphoric acid (H$_3$PO$_4$) and 80.4 grams of water, to which was added 34.4 grams of a hydrated aluminum oxide (a pseudo-boehmite phase, 74.2 wt.% Al$_2$O$_3$, 25.8 wt.% H$_2$O), and stirred until homogeneous. To this mixture was added 110.6 grams of an aqueous solution of 68.2 wt.% N,N'-dimethyl-1,4-diazabicyclo(2,2,2)octane dihydroxide (DDO), and the mixture stirred until homogeneous. The composition of the final reaction mixture in molar oxide ratios was:

1.7DDO:Al$_2$O$_3$:P$_2$O$_5$:40H$_2$O

The reaction mixture was sealed in a lined stainless steel pressure vessel and heated in an oven at 200° C. at autogeneous pressure for 72 hours. The solid reaction product was recovered by filtration, washed with water, and dried in air at 110° C. Chemical analysis showed 9.6 wt.% C, 2.9 wt.% N, 33.2 wt.% Al$_2$O$_3$, 47.6 wt.% P$_2$O$_5$, 19.4 wt.% LOI, giving a product composition in molar oxide ratios of:

0.31DDO:1.0Al$_2$O$_3$:1.03P$_2$O$_5$:0.31H$_2$O

The above product, denominated AlPO$_4$-22, had an X-ray powder diffraction pattern characterized by the following data, wherein "I" is the intensity and "d" the interplanar spacing:

| 2θ | d | 100 × I/Io |
|---|---|---|
| 8.55 | 10.34 | 25 |
| 9.0 | 9.83 | 2 (sh) |
| 9.1 | 9.72 | 57 |
| 11.4 | 7.76 | 1 |
| 12.7 | 6.97 | (sh) |
| 13.0 | 6.81 | 9 |
| 14.6 | 6.07 | 4 |
| 15.6 | 5.68 | 6 |
| 17.3 | 5.13 | 26 |
| 18.5 | 4.80 | 100 |
| 20.65 | 4.30 | 43 |
| 21.4 | 4.15 | 1 (sh) |
| 21.75 | 4.08 | 19 |
| 22.6 | 3.93 | 6 |
| 23.7 | 3.75 | 22 |
| 23.85 | 3.7 | 23 |
| 24.2 | 3.68 | 8 |
| 24.8 | 3.59 | 24 |
| 26.2 | 3.40 | 36 |
| 27.0 | 3.30 | (sh) |
| 27.3 | 3.27 | 20 |
| 27.8 | 3.21 | 8 |
| 28.6 | 3.12 | 10 |
| 29.3 | 3.05 | 30 |
| 30.1 | 2.969 | 8 |
| 31.55 | 2.835 | 16 |

-continued

| 2θ | d | 100 × I/Io |
|---|---|---|
| 32.2 | 2.780 | 2 |
| 33.0 | 2.714 | 2 |
| 33.2 | 2.698 | 2 |
| 34.15 | 2.625 | 2 |
| 34.9 | 2.571 | 11 |
| 35.55 | 2.525 | 5 |
| 37.4 | 2.404 | (sh) |
| 37.6 | 2.392 | 9 |
| 39.1 | 2.304 | 1 |
| 39.25 | 2.295 | 1 |
| 39.75 | 2.268 | 2 |
| 40.35 | 2.235 | 4 |
| 41.2 | 2.191 | 2 |
| 42.1 | 2.146 | 2 |
| 43.7 | 2.071 | 1 |
| 44.3 | 2.045 | 4 |
| 44.7 | 2.027 | 2 |
| 45.2 | 2.006 | 4 |
| 46.4 | 1.957 | 1 |
| 47.0 | 1.933 | 2 |
| 48.4 (sh) | 1.881 | 4 |
| 48.75 | 1.868 | 13 |
| 49.7 | 1.834 | 5 |
| 50.2 | 1.817 | 2 |
| 51.4 | 1.778 | <1 |
| 53.2 | 1.722 | 3 |
| 54.0 | 1.698 | 5 |
| 54.4 | 1.687 | 2 |

(sh = shoulder)

(b) A portion of the solid crystalline product obtained above was calcined in air at about 600° C. for 2 hours. The calcined AlPO₄-22 had an X-ray powder diffraction pattern characterized by the following data:

| 2θ | d | 100 × I/Io |
|---|---|---|
| 8.6 | 10.28 | (sh) |
| 9.15 | 9.65 | 100 |
| 12.6 | 7.03 | } 42 |
| 12.9 | 6.86 | |
| 13.0 | 6.81 | |
| 14.4 | 6.15 | } 21 |
| 14.7 | 6.03 | |
| 17.3 | 5.13 | 50 |
| 18.5 | 4.80 | 92 |
| 20.4 | 4.35 | 64 |
| 21.55 | 4.12 | 23 |
| 22.5 | 3.95 | 11 |
| 23.9 | 3.72 | 34 |
| 24.8 | 3.59 | 18 |
| 25.9 | 3.44 | } 32 |
| 26.1 | 3.41 | (sh) |
| 27.3 | 3.27 | } 24 |
| 27.5 | 3.24 | (sh) |
| 28.4 | 3.14 | 12 |
| 29.1 | 3.07 | 31 |
| 31.2 | 2.867 | } 19 |
| 31.4 | 2.849 | |
| 32.9 | 2.722 | 4 |
| 34.55 | 2.596 | 15 |
| 34.9 | 2.571 | 14 |
| 35.5 | 2.529 | 5 |
| 37.3 | 2.411 | 3 |
| 39.6 | 2.275 | 1 |
| 40.8 | 2.212 | 3 |
| 41.5 | 2.176 | 1 |
| 44.4 | 2.040 | 4 |
| 44.9 | 2.019 | 2 |
| 46.7 | 1.945 | 3 |
| 47.2 | 1.926 | 2 |
| 47.8 | 1.903 | 3 |

-continued

| 2θ | d | 100 × I/Io |
|---|---|---|
| 48.2 | 1.888 | 3 |
| 49.0 | 1.859 | 2 |
| 52.7 | 1.737 | 2 |
| 53.4 | 1.716 | 4 |

The species AlPO₄-22 as herein referred to is a crystalline metallophosphate whose essential framework structure has a chemical composition, expressed in terms of molar ratios of oxides, is $Al_2O_3 : 1.0 \pm 0.2 P_2O_5$ and having a characteristic X-ray powder diffraction pattern which contains at least the d-spacings set forth in Table 21 below:

TABLE 21

| 2θ | d | 100 × I/Io |
|---|---|---|
| 9.1–9.15 | 9.72–9.66 | 57–100 |
| 18.45–18.5 | 4.81–4.80 | 66–100 |
| 20.55–20.65 | 4.32–4.30 | 43–70 |
| 26.1–26.2 | 3.41–3.40 | 36–44 |
| 29.3 | 3.05 | 30–32 |
| 31.55 | 2.835 | 16–29 |

All of the AlPO₄-22 compositions for which the X-ray powder diffraction data has presently been obtained have patterns that are within the generalized pattern of Table 22 below:

TABLE 22

| 2θ | d | 100 × I/Io |
|---|---|---|
| 8.55 | 10.34 | 15–25 |
| 9.0 | 9.83 | (sh) |
| 9.1–9.15 | 9.72–9.66 | 57–100 |
| 11.4 | 7.76 | 0–1 |
| 12.7 | 6.97 | (sh) |
| 12.95–13.0 | 6.83–6.81 | 9–14 |
| 14.5–14.6 | 6.11–6.07 | 3–5 |
| 15.55–15.6 | 5.70–5.68 | 4–6 |
| 17.25–17.3 | 5.14–5.13 | 22–26 |
| 18.45–18.5 | 4.81–4.80 | 66–100 |
| 20.55–20.65 | 4.32–4.30 | 43–70 |
| 21.65–21.75 | 4.10–4.09 | 12–19 |
| 22.6 | 3.93 | 6–7 |
| 23.6–23.7 | 3.77–3.75 | 22 |
| 23.8–23.85 | 3.74–3.73 | 18–23 |
| 24.2 | 3.68 | 8–14 |
| 24.7–24.8 | 3.60–3.59 | 10–24 |
| 26.1–26.2 | 3.41–3.40 | 36–44 |
| 27.0 | 3.30 | (sh) |
| 27.2–27.3 | 3.28–3.27 | 17–20 |
| 27.7–27.8 | 3.22–3.21 | 8–23 |
| 28.6 | 3.12 | 10–14 |
| 29.3 | 3.05 | 30–32 |
| 30.1 | 2.969 | 6–8 |
| 31.55 | 2.835 | 16–29 |
| 32.2 | 2.780 | 0–2 |
| 32.9–33.0 | 2.722–2.714 | 2–3 |
| 33.2–33.3 | 2.698–2.691 | 2–3 |
| 34.1–34.15 | 2.629–2.625 | 2–3 |
| 34.9 | 2.571 | 5–11 |
| 35.55 | 2.525 | 5–8 |
| 37.4 | 2.404 | (sh) |
| 37.5–37.6 | 2.398–2.392 | 6–9 |
| 39.0–39.25 | 2.309–2.295 | 1–2 |
| 39.75 | 2.267 | 0–2 |
| 40.30–40.35 | 2.238–2.235 | 2–3 |
| 41.0–41.2 | 2.201–2.191 | 1–2 |
| 41.9–42.1 | 2.156–2.146 | 2–3 |
| 43.7 | 2.071 | 1–5 |
| 44.2–44.3 | 2.049–2.045 | 3–4 |
| 44.7–44.9 | 2.027–2.019 | 1–2 |
| 45.2–45.3 | 2.006–2.002 | <1–4 |

TABLE 22-continued

| 2θ | d | 100 × I/Io |
|---|---|---|
| 46.2–46.4 | 1.965–1.957 | <1–1 |
| 46.8–47.0 | 1.941–1.933 | <1–2 |
| 48.1–48.4 | 1.892–1.881 | (sh)–6 |
| 48.6–48.75 | 1.873–1.868 | 13–19 |
| 49.6–49.7 | 1.838–1.834 | 4–5 |
| 50.1–50.2 | 1.821–1.817 | 1–2 |
| 51.4 | 1.778 | <1 |
| 53.0–53.2 | 1.728–1.722 | 2–3 |
| 53.8–54.0 | 1.704–1.698 | 5–6 |
| 54.3–54.4 | 1.689–1.687 | 2 |

EXAMPLE 51.

Preparation of AlPO$_4$-25

The crystalline metallophosphate denominated AlPO$_4$-25 is preferably prepared by the thermally induced structural conversion of a less stable crystalline intermediate which is synthesized by hydrothermal crystallization from a reaction gel in a manner similar to that employed to obtain most of the AlPO$_4$-n species of the present invention. This intermediate, identified as AlPO$_4$-21 is readily synthesized using a considerable variety of organic templating agents which are removed from the structure during calcination to produce the stable AlPO$_4$-25.

(a) Preparation of AlPO$_4$-21.

A reaction mixture was prepared by combining 7.7 grams of 85% orthophosphoric acid (H$_3$PO$_4$) and 25.9 grams of water, to which was added 4.6 grams of a pseudo-boehmite phase (74.2 wt.% Al$_2$O$_3$, 25.8 wt.% H$_2$O), and stirred until homogeneous. To this mixture was added 2.4 grams of (CH$_2$)$_4$:NH, (pyrrolidine), and the mixture stirred until homogeneous. The composition of the final reaction mixture in molar oxide ratios was:

1.0(CH$_2$)$_4$:NH:Al$_2$O$_3$:P$_2$O$_5$:40H$_2$O

The reaction mixture was sealed in a stainless steel pressure vessel lined with polytetrafluoroethylene and heated in an oven at 150° C. at autogenous pressure for 150 hours. The solid reaction product was recovered by filtration, washed with water, and dried in air at 110° C. Chemical analysis of the product showed 10.2 wt.-% C, 3.2 wt.-% N, 32.1 wt.% Al$_2$O$_3$, 47.1 wt.% P$_2$O$_5$, 19.8 wt.% LOI, giving a product composition in molar oxide ratios of:

0.67(CH$_2$)$_4$NH:1.00Al$_2$O$_3$:1.05P$_2$O$_5$:0.83H$_2$O

The product was designated AlPO$_4$-21, and had an X-ray powder diffraction pattern characterized by the following data, wherein "I" is the intensity and "d" the interplanar spacing:

| 2θ | d | 100 × I/Io |
|---|---|---|
| 10.0 | 8.845 | 51 |
| 10.5 | 8.425 | 7 |
| 11.3 | 7.830 | 14 |
| 11.8 | 7.500 | 13 |
| 12.2 | 7.255 | 36 |
| 13.2 | 6.707 | 6 |
| 14.2 | 6.237 | 36 |
| 14.6 | 6.067 | 27 |
| 15.9 | 5.574 | 31 |
| 16.8 | 5.277 | 6 |
| 18.5 | 4.796 | 4 |
| 19.6 | 4.529 | 11 |
| 20.4 | 4.353 | 25 |
| 21.1 | 4.210 | 25 |
| 21.3 | 4.171 | 30 |
| 22.6 | 3.934 | 97 |
| 22.8 | 3.900 | 88 |
| 23.7 | 3.754 | 23 |
| 25.1 | 3.548 | 100 |
| 25.8 | 3.453 | 6 |
| 26.2 | 3.401 | 19 |
| 26.6 | 3.351 | 53 |
| 27.6 | 3.232 | 47 |
| 28.2 | 3.164 | 21 |
| 29.0 | 3.079 | 11 |
| 29.4 | 3.038 | 3 |
| 30.6 | 2.921 | 5 |
| 31.0 | 2.885 | 8 |
| 32.0 | 2.797 | 35 |
| 32.6 | 2.747 | 23 |
| 32.9 | 2.722 | 38 |
| 34.0 | 2.637 | 15 |
| 35.2 | 2.550 | 2 |
| 35.9 | 2.501 | 6 |
| 37.2 | 2.417 | 12 |
| 37.8 | 2.380 | 3 |
| 38.8 | 2.321 | 5 |
| 40.2 | 2.243 | 7 |
| 44.4 | 2.040 | 7 |
| 47.6 | 1.910 | 8 |
| 50.8 | 1.797 | 7 |
| 52.0 | 1.759 | 9 |
| 52.6 | 1.740 | 11 |
| 53.2 | 1.722 | 8 |
| 54.0 | 1.698 | 7 |

(b) A procedure similar to that in part (a) above was followed except where indicated in Table E. A portion of the solid product from each reaction was subjected to X-ray analysis and in each case a phase characterized by an X-ray powder diffraction pattern essentially the same as that in part (a) was observed alone or in admixture.

TABLE E

| Example # | Organic Used (R) | R | Al$_2$O$_3$ | P$_2$O$_3$ | H$_2$O | Digestion Time (Hrs.) | Temp. (°C.) |
|---|---|---|---|---|---|---|---|
| (b)1 | (CH$_3$)$_9$N Trimethyl-amine | 1 | 1 | 1 | 50 | 94 | 150 |
| (b)2 | (CH$_2$)$_4$:NH Pyrrolidine | 1 | 1 | 1 | 50 | 166 | 150 |
| (b)3 | C$_6$H$_{14}$N$_2$ 1,4-Dimethyl Piperazine | 1 | 1 | 1 | 50 | 168 | 200 |
| (b)4 | C$_{11}$H$_{26}$N$_2$ 3-(di-n-butyl-amino)-Propylamine | 1 | 1 | 1 | 40 | 168 | 200 |
| (b)5 | C$_7$H$_{16}$N$_2$ N,N,N',N'—tetramethyl-1,3-propane-diamine | 1 | 1 | 1 | 40 | 168 | 200 |
| (b)6 | C$_4$H$_{11}$NO N,N—di-methyl-ethan-olamine | 1 | 1 | 1 | 40 | 336 | 200 |
| (b)7 | n-C$_3$H$_7$NH$_2$ n-Propyl-amine | 1 | 1 | 1 | 50 | 334 | 200 |
| (b)8 | C$_6$H$_{16}$N$_2$ N,N,N',N'—tetramethyl-ethylenedi- | 1 | 1 | 1 | 50 | 168 | 200 |

TABLE E-continued

| Example # | Organic Used (R) | Reaction Mixture Composition | | | | Digestion Time (Hrs.) | Temp. (°C.) |
|---|---|---|---|---|---|---|---|
| | | R | Al₂O₃ | P₂O₃ | H₂O | | |
| (b)9 | amine C₃H₈NO N—Methyl-ethanolamine | 1 | 1 | 1 | 50 | 168 | 200 |

Preparation of AlPO₄-25

(c) A portion of the AlPO₄-21 crystalline product obtained in part (a) was calcined in air at about 600° C. for 2 hours. The calcined product had an X-ray powder diffraction pattern quite different from the starting AlPO₄-21 and is a new and novel microporous aluminophosphate species denominated AlPO₄-25. The X-ray pattern of this species is characterized by the following data:

| 2θ | d | 100 × I/Io |
|---|---|---|
| 7.6 | 11.632 | 3 |
| 9.6 | 9.213 | 83 |
| 10.6 | 8.346 | 1 |
| 11.8 | 7.500 | 14 |
| 12.6 | 7.025 | 3 |
| 15.2 | 5.829 | 100 |
| 19.1 | 4.647 | 71 |
| 21.3 | 4.171 | 84 |
| 22.7 | 3.917 | 17 |
| 23.6 | 3.770 | 8 |
| 24.6 | 3.619 | 6 |
| 25.5 | 3.490 | 43 |
| 26.1 | 3.414 | 14 |
| 28.6 | 3.121 | 10 |
| 29.9 | 2.988 | 3 |
| 31.0 | 2.885 | 23 |
| 33.2 | 2.698 | 8 |
| 35.7 | 2.515 | 7 |
| 37.4 | 2.404 | 8 |
| 37.9 | 2.374 | 8 |
| 43.2 | 2.094 | 3 |
| 53.3 | 1.719 | 3 |

(d) Five AlPO₄-21 samples crystallized in parts (b)1, (b)3, (b)5, (b)7 and (b)9, respectively, were calcined at 500°-600° C. in air and found to convert to the crystal structure characteristic of AlPO₄-25. It is believed all AlPO₄-21 compositions can be converted to AlPO₄-25 in a similar manner.

The species AlPO₄-25 as herein referred to is a crystalline metallophosphate whose essential framework structure has a chemical composition, expressed in terms of molar oxides, is Al₂O₃:1.0±0.2P₂O₅ and having a characteristic X-ray powder diffraction pattern which contains at least the d-spacings set forth in Table 23 below:

TABLE 23

| 2θ | d | 100 × I/Io |
|---|---|---|
| 9.4 | 9.41 | 32–96 |
| 15.0 | 5.91 | 35–76 |
| 18.8–18.9 | 4.72–4.70 | 35–100 |
| 21.1 | 4.21 | 28–100 |
| 22.5 | 3.95 | 16–32 |
| 25.3 | 3.52 | 14–37 |

TABLE 23-continued

| 2θ | d | 100 × I/Io |
|---|---|---|
| 30.8–30.9 | 2.90–2.89 | 20–31 |

EXAMPLE 52

Preparation of AlPO₄-26

A solution of 200 grams 1, 4-dibromobutane in 500° cc of a 4:1 volume mixture of dimethylformamide:methanol (DMF/MeOH) was prepared and cooled to 0° in an ice/water bath. To this was added a solution of 159.4 grams N,N,N',N'-tetramethyl-1,6-hexanediamine in 500 cc 4:1 DMF/MeOH. This mixture was stirred for three days, gradually warming to ambient temperature. The product mass was slurried in diethylether, filtered, washed with ether and dried in air at ambient temperature. The product was a polymeric quaternary ammonium salt, [(C₁₄H₃₂N₂)Br₂]ₓ:

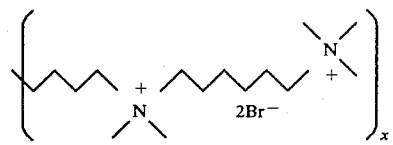

In order to obtain the hydroxide form, 200 grams of the above polymer was dissolved in 800 grams of H₂O and added dropwise over 6 hours to a stirred suspension of 131.4 grams Ag₂O in 1000 grams H₂O. The resulting mixture was stirred overnight and filtered. Chemical analysis of the filtrate showed 1.9 wt.% C, 0.32 wt.% N, and 0.014 wt.% Br, corresponding to an aqueous solution containing 3.0 wt.% of the polymer [(C₁₄H₃₂N₂)(OH)₂]ₓ. The concentration of the polymer in a portion of the filtrate was increased to 12.9 wt.% by removing H₂O at reduced pressure.

A reaction mixture was prepared by combining 101.6 grams of the above aqueous solution containing 12.9 wt.% of the polymeric quaternary ammonium hydroxide with 6.9 grams of a hydrated aluminum oxide (a pseudoboehmite phase, 74.2 wt.% Al₂O₃, 25.8 wt.% H₂O). This mixture was stirred until homogeneous. To this mixture was added 11.5 grams 85 wt.% orthophosphoric acid and the mixture stirred until homogeneous. The composition of the final reaction mixture in molar oxide ratios was:

1.0(C₁₄H₃₂N₂)(OH)₂:Al₂O₃:P₂O₅:105H₂O

The reaction mixture was placed in a sealed stainless steel pressure vessel having an inert liner and heated in an oven at 200° C. at autogenous pressure for 24 hours. The solid reaction product was recovered by filtration, washed with water, and dried in air at 110° C. The resulting AlPO₄-26 product had an X-ray powder diffraction pattern characterized by the following data, wherein "I" is the intensity and "d" the interplanar spacing:

TABLE 24

| 2θ | d | 100 × I/Io |
|---|---|---|
| 8.35 | 10.59 | 100 |
| 9.85 | 8.98 | 14 |
| 10.2 | 8.67 | (sh) |
| 10.55 | 8.38 | 68 |

TABLE 24-continued

| 2θ | d | 100 × I/Io |
|---|---|---|
| 11.8 | 7.50 | 1 |
| 13.5 | 6.56 | 8 |
| 14.5 | 6.11 | 6 |
| 15.45 | 5.73 | 3 |
| 16.8 | 5.28 | 10 |
| 17.65 | 5.02 | 15 |
| 18.05 | 4.91 | 18 |
| 19.0 | 4.67 | 1 |
| 19.9 | 4.46 | 11 |
| 20.3 | 4.37 | 1 |
| 21.65 | 4.10 | 4 |
| 22.25 | 3.99 | 31 |
| 23.05 | 3.86 } | 74 |
| 22.9 | 3.88 } | |
| 24.7 | 3.60 | 6 |
| 25.25 | 3.527 | 10 |
| 25.85 | 3.446 | 2 |
| 27.2 | 3.278 | 10 |
| 27.45 | 3.249 | 6 |
| 27.95 | 3.192 | 6 |
| 29.2 | 3.058 | 4 |
| 29.7 | 3.008 | 1 |
| 30.45 | 3.936 | 9 |
| 30.9 | 2.8938 } | 12 |
| 31.1 | 2.875 } | |
| 31.6 | 2.83 | 2 |
| 32.25 | 2.776 | 8 |
| 32.7 | 2.739 | 1 |
| 33.8 | 2.652 | 1 |
| 34.3 | 2.614 | 6 |
| 35.0 | 2.564 | 1 |
| 35.4 | 2.536 | 1 |
| 36.15 | 2.485 | <1 |
| 36.4 | 2.468 | <1 |
| 37.45 | 2.401 | 2 |
| 38.6 | 2.332 | <1 |
| 39.0 | 2.309 | <1 |
| 39.4 | 2.287 | 1 |
| 40.0 | 2.254 | <1 |
| 40.5 | 2.227 | 2 |
| 41.3 | 2.186 | 2 |
| 42.4 | 2.132 | 2 |
| 43.1 | 2.099 | 4 |
| 44.2 | 2.049 | <1 |
| 45.7 | 1.985 | <1 |
| 46.1 | 1.969 | 1 |
| 47.8 | 1.903 | 1 |
| 48.15 | 1.890 | 2 |
| 49.1 | 1.855 | 2 |
| 49.7 | 1.834 | <1 |
| 50.7 | 1.801 | <1 |
| 51.4 | 1.778 | 2 |
| 52.5 | 1.743 | 1 |
| 52.9 | 1.731 | <1 |
| 53.7 | 1.707 | 2 |
| 54.4 | 1.687 | 3 |
| 55.2 | 1.664 | 1 |

The species AlPO$_4$-26 as herein referred to is a crystalline metallophosphate whose essential framework structure has a chemical composition, expressed in terms of molar ratios of oxides is:

Al$_2$O$_3$:1±0.2P$_2$O$_5$ and having an X-ray powder diffraction pattern essentially as set forth in TABLE 24.

EXAMPLE 53

Preparation of AlPO$_4$-28

The crystalline metallophosphate denominated AlPO$_4$-28 is preferably prepared by the thermally induced structural conversion of a less stable crystalline intermediate which is synthesized by hydrothermal crystallization from a reaction gel in a manner similar to that employed to obtain most of the AlPO$_4$-n species of the present invention. This intermediate, identified as AlPO$_4$-23 is readily synthesized using pyrrolidine as the templating agent which is removed from the structure during calcination to produce the stable AlPO$_4$-28.

(a) Preparation of AlPO$_4$-23

A reaction mixture was prepared by combining 23.1 grams of 85% orthophosphoric acid (H$_3$PO$_4$) and 77.6 grams of water, to which was added 13.8 grams of a hydrated aluminum oxide (a pseudo-boehmite phase, 74.2 wt.% Al$_2$O$_3$, 25.8 wt.% H$_2$O), and stirred until homogeneous. To this mixture was added 7.1 grams of (CH$_2$)$_4$:NH (pyrrolidine), and the mixture stirred until homogeneous. The composition of the final reaction mixture in molar oxide ratios was:

1.0(CH$_2$)$_4$NH:Al$_2$O$_3$:P$_2$O$_5$:50H$_2$O

The reaction mixture was placed in a sealed stainless steel pressure vessel lined with an inert plastic material and heated in an oven at 200° C. at autogenous pressure for 91 hours. The solid reaction product was recovered by filtration, washed with water, and dried in air at 110° C. Chemical analysis showed 9.9 wt.% C, 31. wt.% N, 32.8 wt.% Al$_2$O$_3$, 47.5 wt.% P$_2$O$_5$, 19.3 wt.% LOI, giving a product composition in molar oxide ratios of:

0.64(CH$_2$)$_4$:NH:1.00Al$_2$O$_3$:1.04P$_2$O$_4$:0.79H$_2$O

The product denominated AlPO$_4$-23 had an X-ray powder diffraction pattern characterized by the following data, wherein "I" is the intensity and "d" the interplanar spacing:

| 2θ | d | 100 × I/Io |
|---|---|---|
| 7.4 | 11.946 | 47 |
| 10.3 | 8.588 | 24 |
| 10.7 | 8.268 | 64 |
| 11.6 | 7.628 | 54 |
| 11.9 | 7.437 | 43 (sh) |
| 13.4 | 6.607 | 4 |
| 14.7 | 6.026 | 4 |
| 15.0 | 5.906 | 6 |
| 16.8 | 5.277 | 6 |
| 19.0 | 4.671 | 21 |
| 20.4 | 4.353 | 28 |
| 21.3 | 4.171 | 100 |
| 23.2 | 3.834 | 65 |
| 24.0 | 3.708 | 9 |
| 24.5 | 3.633 | 6 (sh) |
| 26.2 | 3.401 | 16 |
| 27.2 | 3.278 | 11 |
| 27.8 | 3.209 | 12 |
| 28.6 | 3.121 | 36 |
| 29.6 | 3.018 | 30 |
| 30.8 | 2.903 | 11 |
| 32.2 | 2.780 | 74 |
| 33.8 | 2.652 | 2 |
| 34.9 | 2.571 | 7 |
| 36.2 | 2.481 | 8 |
| 37.4 | 2.404 | 4 |
| 39.2 | 2.298 | 2 |
| 40.7 | 2.217 | 7 |
| 43.3 | 2.090 | 4 |
| 48.2 | 1.888 | 8 |
| 49.8 | 1.831 | 4 |
| 51.8 | 1.765 | 2 |
| 52.8 | 1.734 | 5 |

(b) Preparation of AlPO4-28

A portion of the AlPO4-23 composition prepared in part (a), supra, was calcined in air at about 600° C. for 2 hours. The calcined product was crystalline but had an X-ray powder diffraction pattern substantially different from the precursor material. It is apparent that the calcination procedure converted the original AlPO4-23 to a new microporous aluminophosphate species of the present invention, namely AlPO4-28. The X-ray powder diffraction pattern of the AlPO4-28 product is as follows:

| 2θ | d | 100 × I/Io |
|---|---|---|
| 7.9 | 11.191 | 41 |
| 9.9 | 8.934 | 7 |
| 12.2 | 7.255 | 100 |
| 13.3 (sh) | 6.657 | 22 |
| 15.7 | 5.644 | 7 |
| 18.6 | 4.770 | 47 |
| 19.2 (sh) | 4.623 | 25 |
| 21.0 | 4.230 | 9 |
| 21.9 | 4.058 | 30 |
| ~23.5 | 3.786 | 7 |
| 25.4 | 3.507 | 20 |
| 26.1 | 3.414 | 13 |
| 27.0 | 3.302 | 16 |
| 29.7 | 3.008 | 13 |
| 30.9 | 2.894 | 13 |
| 32.1 | 2.788 | 11 |
| 35.4 | 2.536 | 6 |
| 36.4 | 2.468 | 2 |

The species AlPO4-28 as herein referred to is a crystalline metallophosphate whose essential framework structure has a chemical composition, expressed in terms of molar ratios of oxides, is $$Al_2O_3 : 1.0 \pm 0.2 P_2O_5$$

and having a characteristic X-ray powder diffraction pattern which contains at least the d-spacings set forth in Table 25 below:

TABLE 25

| 2θ | d | 100 × I/Io |
|---|---|---|
| 7.9 | 11.19 | 41 |
| 12.2 | 7.26 | 100 |
| 18.6 | 4.77 | 47 |
| 21.9 | 4.06 | 30 |
| 25.4 | 3.51 | 20 |
| 27.0 | 3.30 | 16 |

EXAMPLE 54

Preparation of AlPO4-31

(a) A reaction mixture was prepared by dispersing 164.8 grams of a pseudo-boehmite phase (74.2 wt.% Al2O3, 25.8 wt.% H2O) in 715.2 grams of water, to which was added 276.7 grams of 85% orthophosphoric acid, and stirred until homogeneous. To this mixture was added 121.4 grams of di-(n-propyl) amine (Pr2NH), and the mixture stirred until homogeneous. The composition of the final reaction mixture in molar oxide ratios was:

$$1.0 Pr_2NH : Al_2O_3 : P_2O_5 : 40 H_2O$$

The reaction mixture was sealed in a stainless steel pressure vessel lined with polytetrafluoroethylene and heated in an oven at 200° C. at autogeneous pressure for 46 hours. The solid reaction product was recovered by repeated centrifugation and washing with H2O, and dried in air at room temperature. Chemical analysis of the reaction product showed 4.7 wt.% C, 0.85 wt.% N, 37.4 wt.% Al2O3, 51.6 wt.% P2O5, 10.3 wt.% LOI, giving a product composition expressed in molar oxide ratios of $$0.18 Pr_2NH : 1.00 Al_2O_3 : 0.99 P_2O_5 : 0.56 H_2O$$

The above product, denominated AlPO4-31, had an X-ray powder diffraction pattern characterized by the following data, wherein "I" is the intensity and "d" the interplanar spacing:

TABLE 26

| 2θ | d | 100 × I/Io |
|---|---|---|
| 8.5 | 10.40 | 85 |
| 9.5 | 9.31 | 12 |
| 13.35 | 6.63 | 6 |
| 13.8 | 6.42 | 2 |
| 14.8 | 5.99 | 2 |
| 15.7 | 5.64 | 6 |
| 17.1 | 5.19 | 7 |
| 18.3 | 4.85 | 7 |
| 20.0 sh | 4.44 | — |
| 20.3 | 4.37 | 48 |
| 21.1 | 4.21 | 28 |
| 21.8 | 4.08 | 26 |
| 22.6 | 3.93 | 100 |
| 23.2 sh | 3.83 | — |
| 24.8 | 3.59 | 7 |
| 25.6 | 3.48 | 8 |
| 27.7 | 3.22 | 11 |
| 28.3 | 3.15 | 7 |
| 29.6 | 3.02 | 9 |
| 29.9 | 2.99 | 9 |
| 31.4 sh | 2.85 | |
| 31.6 | 2.83 | 14 |
| 35.2 | 2.55 | 10 |
| 35.8 | 2.51 | 6 |
| 38.0 | 2.37 | 8 |
| 40.0 | 2.25 | 4 |

(b) A portion of the solid crystalline product obtained above was calcined to a temperature of 1000° C. This calcined material had an X-ray powder diffraction pattern essentially identical to that of part (a).

EXAMPLE 55

(a) Adsorption capacities of AlPO4-5 (prepared in Ex. 3(b) supra) were measured using a standard McBain-Bakr gravimetric adsorption apparatus. The following data were obtained on a sample activated at 350° C.:

| | Kinetic Diameter, Å | Pressure, Torr | Temp., °C. | Wt. % Adsorbed |
|---|---|---|---|---|
| O2 | 3.46 | 97 | −183 | 12.6 |
| O2 | 3.46 | 750 | −183 | 17.0 |
| Neopentane (C4F9)3N(after | 6.2 | 102 | 24 | 5.5 |
| 4 hours) | 10 | 0.073 | 24 | 1.2 |
| H2O | 2.65 | 4.6 | 24 | 4.6 |
| H2O | 2.65 | 18.5 | 23 | 26.4 |

The pore size of the calcined product is greater than 6 and less than 10 Å as shown by adsorption of neopentane, kinetic diameter of 6.2 Å, and nil adsorption of (C4F9)3N, kinetic diameter of 10 Å.

(b) Adsorption capacities of AlPO4-5 (prepared in Example 2(b) supra) were measured using a standard McBain-Bakr gravimetric adsorption apparatus. The following data were obtained on a sample activated at 350° C.:

|  | Kinetic Diameter, Å | Pressure, Torr | Temp., °C. | Wt. % Adsorbed |
|---|---|---|---|---|
| $O_2$ | 3.46 | 99 | −183 | 13.3 |
| $O_2$ | 3.46 | 730 | −183 | 18.3 |
| Cyclohexane | 6.0 | 54 | 24 | 9.5 |
| Neopentane | 6.2 | 102 | 24 | 4.8 |
| $H_2O$ | 2.65 | 4.6 | 24 | 3.9 |
| $H_2O$ | 2.65 | 21.0 | 24 | 29.8 |

The pore size of the calcined product is greater than 6.2 Å, as shown by adsorption of neopentane, kinetic diameter of 6.2 Å.

(c) Adsorption capacities of AlPO$_4$-5 (prepared in a manner similar to that of example 2(b) supra) were measured using a standard McBain-Bakr gravimetric adsorption apparatus. The following data were obtained on a sample activated at 350° C.:

|  | Kinetic Diameter Å | Pressure, torr | Temp., °C. | Wt. % Adsorbed |
|---|---|---|---|---|
| $O_2$ | 3.46 | 105 | −183 | 14.6 |
| $O_2$ | 3.46 | 705 | −183 | 21.3 |
| Neopentane | 6.2 | 103 | 25 | 6.5 |
| $H_2O$ | 2.65 | 4.6 | 25 | 6.5 |
| $H_2O$ | 2.65 | 20.7 | 25 | 32.6 |

EXAMPLE 56

Adsorption capacities of AlPO$_4$-28 (prepared in Example 53(b), supra) were measured using a standard McBain-Bakr gravimetric adsorption apparatus. The following data were obtained on a sample activated at 350° C.:

|  | Kinetic Diameter, Å | Pressure, Torr | Temp., °C. | Wt. % Adsorbed |
|---|---|---|---|---|
| $O_2$ | 3.46 | 103 | −183 | 1.0 |
| $O_2$ | 3.46 | 761 | −183 | 2.5 |
| n-Hexane | 4.3 | 28 | 24 | 0.4 |
| Neopentane | 6.2 | 310 | 24 | 0.5 |
| $H_2O$ | 2.65 | 4.6 | 24 | 11.1 |
| $H_2O$ | 2.65 | 20.0 | 24 | 21.4 |

The pore size of the calcined product is >2.65 Å, and <3.46 Å, as shown by adsorption of $H_2O$, kinetic diameter of 2.65 Å, and nil adsorption of $O_2$, kinetic diameter of 3.46 Å.

EXAMPLE 57

Adsorption capacities of AlPO$_4$-25 (prepared in Ex. 52(c), supra) were measured using a standard McBain Bakr gravimetric adsorption apparatus. The following data were obtained on a sample activated at 350° C.:

|  | Kinetic Diameter, Å | Pressure, Torr | Temp., °C. | Wt. % Adsorbed |
|---|---|---|---|---|
| $O_2$ | 3.46 | 103 | −183 | 4.9 |
| $O_2$ | 3.46 | 761 | −183 | 5.9 |
| n-Hexane | 4.3 | 28 | 25 | 0.3 |
| Neopentane | 6.2 | 310 | 25 | 0.4 |
| $H_2O$ | 2.65 | 4.6 | 25 | 4.4 |
| $H_2O$ | 2.65 | 20.0 | 25 | 16.6 |

The pore size of the calcined product is >3.4 Å and <4.3 Å, as shown by adsorption of $O_2$, kinetic diameter of 3.46 Å, and nil adsorption of n-hexane, kinetic diameter of 4.3 Å.

EXAMPLE 58

Adsorption capacities of AlPO$_4$-20 (prepared as in Example 47(b) supra) were measured using a standard McBain-Bakr gravimetric adsorption apparatus. The following data were obtained on a sample activated at 350° C.:

|  | Kinetic Diameter, Å | Pressure, Torr | Temp., °C. | Wt. % Adsorbed |
|---|---|---|---|---|
| $O_2$ | 3.46 | 97 | −183 | 2.7 |
| $O_2$ | 3.46 | 750 | −183 | 11.5 |
| n-Hexane | 4.3 | 45 | 24 | 1.7 |
| neopentane | 6.2 | 303 | 24 | 1.5 |
| Cyclohexane | 6.0 | 11 | 24 | 1.3 |
| $H_2O$ | 2.65 | 4.6 | 24 | 22.6 |
| $H_2O$ | 2.65 | 18.5 | 24 | 37.2 |

The pore size of the calcined product is ca. 3 Å, as shown by adsorption of $H_2O$, kinetic diameter of 2.65 Å, and low adsorption at low partial pressures of $O_2$, kinetic diameter of 3.46 Å.

EXAMPLE 59

Adsorption capacities of AlPO$_4$-17 (prepared in Ex. 42(c) supra) using a standard McBain-Bakr gravimetric adsorption apparatus. The following data were obtained on a sample activated at 350° C.:

|  | Kinetic Diameter, Å | Pressure Torr | Temp., °C. | Wt. % Adsorbed |
|---|---|---|---|---|
| $O_2$ | 3.46 | 102 | −183 | 22.2 |
| $O_2$ | 3.46 | 724 | −183 | 23.1 |
| n-Hexane | 4.3 | 45 | 23 | 7.7 |
| Isobutane | 5.0 | 101 | 22 | 0.2 |
| Neopentane | 6.2 | 308 | 23 | 0.3 |
| $H_2O$ | 2.65 | 4.6 | 22 | 24.9 |
| $H_2O$ | 2.65 | 18 | 22 | 27.8 |

The pore size of the calcined product is >4.3 Å and <5.0 Å, as shown by adsorption of n-hexane, kinetic diameter of 4.3 Å, and nil adsorption of isobutane, kinetic diameter of 5.0 Å.

EXAMPLE 60

Adsorption capacities of AlPO$_4$-16 (prepared in Example 41(d) supra) were measured using a standard McBain-Bakr gravimetric adsorption apparatus. The following data were obtained on a sample activated at 350° C.:

|  | Kinetic Diameter, Å | Pressure Torr | Temp., °C. | Adsorbed |
|---|---|---|---|---|
| $O_2$ | 3.46 | 101 | −183 | 1.2 |
| $O_2$ | 3.46 | 755 | −183 | 11.6 |
| n-Butane | 4.3 | 768 | 24 | 2.0 |
| Neopentane | 6.2 | 301 | 25 | 1.4 |
| $H_2O$ | 2.65 | 4.6 | 24 | 19.0 |
| $H_2O$ | 2.65 | 20 | 24 | 36.3 |

The pore size of the calcined product is >2.65 and <3.46 Å, as shown by adsorption of $H_2O$, kinetic diameter of 2.65 Å, and low adsorption of $O_2$ at low partial pressures, kinetic diameter of 3.46 Å.

EXAMPLE 61

Adsorption capacities of AlPO$_4$-14 (prepared in Ex. 39(b) supra) using a standard McBain-Bakr gravimetric adsorption apparatus. The following data were obtained on a sample activated at 350° C.:

| Adsorbate | Kinetic Diameter, Å | Pressure, Torr | Temp., °C. | Wt. % Adsorbed |
|---|---|---|---|---|
| O$_2$ | 3.46 | 102 | −183 | 15.53 |
| O$_2$ | 3.46 | 763 | −183 | 21.56 |
| n-Hexane | 4.3 | 45 | 26 | 0.25 |
| neopentane | 6.2 | 499 | 24 | 0.37 |
| H$_2$O | 2.65 | 4.6 | 24 | 21.46 |
| H$_2$O | 2.65 | 21.0 | 24 | 28.66 |
| N$_2$ | 3.64 | 100 | −196 | 11.28 |
| N$_2$ | 3.64 | 747 | −196 | 14.99 |

The pore size of the calcined product is >3.64 Å and <4.3 Å as shown by adsorption of N$_2$, kinetic diameter of 3.64 Å, and nil adsorption of n-hexane, kinetic diameter of 4.3 Å.

EXAMPLE 62-A

Adsorption capacities of AlPO$_4$-8 (prepared as in Example 29, supra) using a standard McBain-Bakr gravimetric adsorption apparatus. The following data were obtained on a sample activated at 350° C.:

| | Kinetic Diameter, Å | Pressure Torr | Temp., °C. | Wt. % Adsorbed |
|---|---|---|---|---|
| O$_2$ | 3.46 | 101 | −183 | 8.9 |
| O$_2$ | 3.46 | 755 | −183 | 18.6 |
| n-Butane | 4.3 | 768 | 24 | 5.0 |
| Neopentane | 6.2 | 501 | 24 | 4.5 |
| (C$_4$F$_9$)$_3$N (After 4 hours) | 10 | 0.073 | 25 | 8.2 |
| H$_2$O | 2.65 | 4.6 | 24 | 18.5 |
| H$_2$O | 2.65 | 20.0 | 24 | 31.9 |

The pore size of the calcined product is greater than 6.2 Å, as shown by adsorption of neopentane, kinetic diameter of 6.2 Å.

EXAMPLE 62-B

Adsorption capacities of AlPO$_4$-31 (prepared as in Example 54(b) supra except that product was calcined to a temperature of 600° C.) were measured using a standard McBain-Bakr gravimetric adsorption apparatus. The following data were obtained on a sample activated at 350° C.:

| | Kinetic Diameter, Å | Pressure, Torr | Temp., °C. | Wt. % Adsorbed |
|---|---|---|---|---|
| O$_2$ | 3.46 | 99 | −183 | 8.1 |
| O$_2$ | 3.46 | 711 | −183 | 11.5 |
| Butane | 4.3 | 107 | 24 | 4.0 |
| Cyclohexane | 6.0 | 54 | 24 | 5.3 |
| Neopentane | 6.2 | 109 | 24 | 3.1 |
| H$_2$O | 2.65 | 4.6 | 24 | 5.3 |
| H$_2$O | 2.65 | 14.0 | 24 | 13.9 |

The pore size is larger than 6.2 Å as shown by the adsorption of neopentane.

EXAMPLE 63

A portion of the crystalline AlPO$_4$-11 product of Example 32(a) supra was calcined in air from 200° C. to 500° C. over a period of 1 hour, followed by heating at 500° C. for 2 hours.

Adsorption capacities were measured on this calcined product using a standard McBain-Bakr gravimetric adsorption apparatus. The following data were obtained on a sample activated at 350° C.:

| Adsorbate | Kinetic Diameter, Å | Pressure Torr | Temp., °C. | Wt. % Adsorbed |
|---|---|---|---|---|
| O$_2$ | 3.46 | 101 | −183 | 9.22 |
| O$_2$ | 3.46 | 755 | −183 | 10.7 |
| N—butane | 4.3 | 304 | 24 | 4.35 |
| Isobutane | 5.0 | 502 | 24 | 4.71 |
| Neopentane | 6.2 | 301 | 24 | 1.22 |
| Cyclohexane | 6.0 | 30 | 24 | 5.30 |
| H$_2$O | 2.65 | 4.6 | 24 | 11.8 |
| H$_2$O | 2.65 | 20.0 | 24 | 16.4 |

The pore size of the calcined product is greater than 6.0 Å and less than 6.2 Å, as shown by adsorption of cyclohexane, kinetic diameter of 6.0 Å, and nil adsorption of neopentane, kinetic diameter of 6.2 Å.

EXAMPLE 64

Adsorption capacities of AlPO$_4$-18 (prepared in Example 46(b) supra) were measured using a standard McBain-Bakr gravimetric adsorption apparatus. The following data were obtained on a sample activated at 350° C.:

| | Kinetic Diameter, Å | Pressure, torr | Temp. °C. | Wt. % Adsorbed |
|---|---|---|---|---|
| O$_2$ | 3.46 | 130 | −183 | 23.0 |
| O$_2$ | 3.46 | 697 | −183 | 27.9 |
| n-Butane | 4.3 | 718 | 24 | 16.2 |
| iso-Butane | 5.0 | 101 | 24 | 0.1 |
| H$_2$O | 2.65 | 4.6 | 24 | 30.3 |
| H$_2$O | 2.65 | 21.0 | 24 | 36.9 |

The pore size of the calcined product is 4.3 and 5.0 Å, as shown by adsorption of n-butane and nil adsorption of iso-butane at low partial pressure.

Somewhat surprisingly the aluminophosphate compositions of the present invention are found to be strongly hydrophilic. All species are observed to adsorb water preferentially over common hydrocarbon molecules such as paraffins, olefins and benzenoid aromatic species, e.g., benzene, xylenes and cumene. Thus the present aluminophosphates as a class are useful as desiccants in such adsorption separation/purification processes as natural gas drying, cracked gas drying. Water is also preferentially adsorbed over the so-called permanent gases such as carbon dioxide, nitrogen, oxygen and hydrogen. These aluminophosphates are therefore suitably employed in the drying of reformer hydrogen streams and in the drying of oxygen, nitrogen or air prior to liquefaction. In this respect the adsorptive properties of the present aluminophosphates appears to be quite similar to those of the low silica aluminosilicate zeolites, despite the fact that they exhibit essentially no ion-exchange capacity—a quintessential property of zeolites.

The adsorptive properties of the present AlPO$_4$-n compositions are illustrated by the data set forth in Table F and Table G below.

TABLE F

Static Drying of Moist Air at Room Temperature

| Sample | % Humidity Initial | % Humidity Final | Contact Time, hours |
|---|---|---|---|
| Zeolite 4A | 60 | 21 | 3 |
| Zeolite 5A | 54 | 5 | 16 |
| Silica Gel | 56 | 18 | 16 |
| $AlPO_4$-5 | 55 | 29 | 4 |
| $AlPO_4$-8 | 60 | 21 | 3.5 |
| $AlPO_4$-8 | 61 | 19 | 18 |
| $AlPO_4$-11 | 57 | 29 | 5.5 |
| $AlPO_3$-14 | 56 | 19 | 3.0 |
| $AlPO_4$-16 | 70 | 22 | 3.0 |
| $AlPO_4$-16 | 56 | 14 | 72 |
| $AlPO_4$-17 | 63 | 24 | 18.5 |
| $AlPO_4$-20 | 60 | 17 | 16 |
| $AlPO_4$-28 | 56 | 7 | 17.5 |
| $AlPO_4$-25 | 56 | 25 | 18.5 |
| $AlPO_4$-9 | 51 | 29 | 23 |
| $AlPO_4$-18 | 56 | 19 | 24 |
| $AlPO_4$-31 | 51 | 24 | 19 |

To illustrate the hydrophilic character of the $AlPO_4$-n compositions in contact with an aqueous organic solution, dehydrated samples of $AlPO_4$ compounds and prior known comparison adsorbent, each weighing 0.5 grams were placed in 2 grams of a solution of 4 vol.-% $H_2O$ and 96 vol.-% 2-butanone at ambient room temperature and agitated moderately for 2 hours. Thereafter the residual solution and the adsorbent were analyzed for water content. The results appear below:

TABLE G

| Adsorbent | % Water Removal from Solution | % Loading** |
|---|---|---|
| $AlPO_4$-5 | 55 | 23 |
| $AlPO_4$-8 | 74 | 45 |
| $AlPO_4$-11 | 21 | 23 |
| $AlPO_4$-14 | >80 | >45 |
| $AlPO_4$-16 | >80 | >45 |
| $AlPO_4$-17 | 77 | 41 |
| $AlPO_4$-20 | 87 | 58 |
| Zeolite NaY | 80 | 37 |
| Silica Gel | 28 | — |
| Silicalite* | −5 | — |

*U.S. Pat. No. 4,061,724
**Percent of maximum theoretical capacity

The present $AlPO_4$-n compositions exhibit novel surface selectivity characteristics which render them useful as catalyst or catalyst bases in a number of hydrocarbon conversion and oxidative combustion reactions. They can be impregnated or otherwise loaded with catalytically active metals by methods well known in the art and used, for example, in fabricating catalysts compositions having silicalite or alumina bases. Of the general class, those species having pores larger than about 5 A are preferred.

Among the hydrocarbon conversion reactions catalyzed by $AlPO_4$-n compositions are cracking, hydrocracking, alkylation of both the aromatic and isoparaffin types, isomerization including xylene isomerization, polymerization, reforming, hydrogenation, dehydrogenation, transalkylation, dealkylation and hydration.

Using $AlPO_4$-n catalysts compositions which contain a hydrogenation promoter such as platinum or palladium, heavy petroleum residual stocks, cyclic stocks and other hydrocrackable charge stocks can be hydrocracked at temperatures in the range of 400° F. to 825° F. using molar ratios of hydrogen to hydrocarbon in the range of between 2 and 80, pressures between 10 and 3500 p.s.i.g., and a liquid hourly spaced velocity (LHSV) of from 0.1 to 20, preferably 1.0 to 10.

The $AlPO_4$-n catalyst compositions employed in hydrocracking are also suitable for use in reforming processes in which the hydrocarbon feedstocks contact the catalyst at temperatures of from about 700° F. to 1000° F., hydrogen pressures of from 100 to 500 p.s.i.g., LHSV values in the range of 0.1 to 10 and hydrogen to hydrocarbon molar ratios in the range of 1 to 20, preferably between 4 and 12.

These same catalysts, i.e. those containing hydrogenation promoters, are also useful in hydroisomerization processes in which feedstocks such as normal paraffins are converted to saturated branched chain isomers. Hydroisomerization is carried out at a temperature of from about 200° F. to 600° F., preferably 300° F. to 550° F. with an LHSV value of from about 0.2 to 1.0. Hydrogen is supplied to the reactor in admixture with the hydrocarbon feedstock in molar proportions (H/Hc) of between 1 and 5.

At somewhat higher temperatures, i.e. from about 650° F. to 1000° F., preferably 850° F. to 950° F. and usually at somewhat lower pressures within the range of about 15 to 50 p.s.i.g., the same catalyst compositions are used to hydroisomerize normal paraffins. Preferably the paraffin feedstock comprises normal paraffins having a carbon number range of $C_7$–$C_{20}$. Contact time between the feedstock and the catalyst is generally relatively short to avoid undesireable side reactions such as olefin polymerization and paraffin cracking. LHSV values in the range of 0.1 to 10, preferably 1.0 to 6.0 are suitable.

The unique crystal structure of the present $AlPO_4$ catalysts and their total lack of alkali metal content favor their use in the conversion of alkylaromatic compounds, particularly the catalytic disproportionation of toluene, ethylene, trimethyl benzenes, tetramethyl benzenes and the like. In the disporportionation process isomerization and transalkylation can also occur. Group VIII noble metal adjuvents alone or in conjunction with Group VI-B metals such as tungsten, molybdenum and chromium are preferably included in the catalyst composition in amounts of from about 3 to 15 weight-% of the overall composition. Extraneous hydrogen can, but need not be present in the reaction zone which is maintained at a temperature of from about 400° to 750° F., pressures in the range of 100 to 2000 p.s.i.g. and LHSV values in the range of 0.1 to 15.

Catalytic cracking processes are preferably carried out with $AlPO_4$-n compositions using feedstocks such as gas oils, heavy naphthas, deasphalted crude oil residua etc. with gasoline being the principal desired product. Temperature conditions of 850° to 1100° F., LHSV values of 0.5 to 10 and pressure conditions of from about 0 to 50 p.s.i.g. are suitable.

Dehydrocyclization reactions employing paraffinic hydrocarbon feedstocks, preferably normal paraffins having more than 6 carbon atoms, to form benzene, xylenes, toluene and the like are carried out using essentially the same reaction conditions as for catalytic cracking. For these reactions it is preferred to use the $AlPO_4$-n catalyst in conjunction with a Group VIII non-noble metal cation such as cobalt and nickel.

In catalytic dealkylation wherein it is desired to cleave paraffinic side chains from aromatic nuclei without substantially hydrogenating the ring structure, relatively high temperatures in the range of about 800°–1000° F. are employed at moderate hydrogen pressures of about 300-1000 p.s.i.g., other conditions being similar to those described above for catalytic hydrocracking. Preferred catalysts are of the same type described above in connection with catalytic dehydrocyclization. Particularly desirable dealkylation reactions contemplated herein include the conversion of methylnaphthalene to naphthalene and toluene and/or xylenes to benzene.

In catalytic hydrofining, the primary objective is to promote the selective hydrodecomposition of organic sulfur and/or nitrogen compounds in the feed, without substantially affecting hydrocarbon molecules therein. For this purpose it is preferred to employ the same general conditions described above for catalytic hydrocracking, and catalysts of the same general nature described in connection with dehydrocyclization operations. Feedstocks include gasoline fractions, kerosenes, jet fuel fractions, diesel fractions, light and heavy gas oils, deasphalted crude oil residua and the like any of which may contain up to about 5 weight-percent of sulfur and up to about 3 weight-percent of nitrogen.

Similar conditions can be employed to effect hydrofining, i.e., denitrogenation and desulfurization, of hydrocarbon feeds containing substantial proportions of organonitrogen and organosulfur compounds. It is generally recognized that the presence of substantial amounts of such constituents markedly inhibits the activity of catalysts for hydrocracking. Consequently, it is necessary to operate at more extreme conditions when it is desired to obtain the same degree of hydrocracking conversion per pass on a relatively nitrogenous feed than are required with a feed containing less organonitrogen compounds. Consequently, the conditions under which denitrogenation, desulfurization and/or hydrocracking can be most expeditiously accomplished in any given situation are necessarily determined in view of the characterisics of the feedstocks in particular the concentration of organonitrogen compounds in the feedstock. As a result of the effect of organonitrogen compounds on the hydrocracking activity of these compositions it is not at all unlikely that the conditions most suitable for denitrogenation of a given feedstock having a relatively high organonitrogen content with minimal hydrocracking, e.g., less than 20 volume percent of fresh feed per pass, might be the same as those preferred for hydrocracking another feedstock having a lower concentration of hydrocracking inhibiting constituents e.g., organonitrogen compounds. Consequently, it has become the practice in this art to establish the conditions under which a certain feed is to be contacted on the basis of preliminary screening tests with the specific catalyst and feedstock.

Isomerization reactions are carried out under conditions similar to those described above for reforming, using somewhat more acidic catalysts. Olefins are preferably isomerized at temperatures of 500°-900° F., while paraffins, naphthenes and alkyl aromatics are isomerized at temperatures of 700°-1000° F. Particularly desirable isomerization reactions contemplated herein include the conversion of n-heptane and/or n-octane to isoheptanes, iso-octanes, butane to iso-butane, methylcyclopentane to cyclohexane, meta-xylene and/or ortho-xylene to paraxylene, 1-butene to 2-butene and/or isobutene, n-hexene to isohexene, cyclohexene to methylcyclopentene etc. The preferred cation form is a combination of the AlPO$_4$-n with polyvalent metal compounds (such as sulfides) of metals of Group II-A, Group II-B and rare earth metals. For alkylation and dealkylation processes the AlPO$_4$-n compositions having pores of at least 5 A are preferred. When employed for dealkylation of alkyl aromatics, the temperature is usually at least 350° F. and ranges up to a temperature at which substantial cracking of the feedstock or conversion products occurs, generally up to about 700° F. The temperature is preferably at least 450° F. and not greater than the critical temperature of the compound undergoing dealkylation. Pressure conditions are applied to retain at least the aromatic feed in the liquid state. For alkylation the temperature can be as low as 250° F. but is preferably at least 350° F. In alkylation benzene, toluene and xylene, the preferred alkylating agent are olefins such as ethylene and propylene.

What is claimed is:

1. Process for separating polar molecular species having effective molecular diameters of less than about 10 Angstroms from mixture with less polar species by contacting said mixture with at least one crystalline aluminophosphate, said aluminophosphate being at least partially dehydrated, having a pore diameter large enough to adsorb the more polar molecular species, and having a framework structure whose chemical composition expressed in terms of mole ratios of oxides is:

Al$_2$O$_3$:1.0±0.2 P$_2$O$_5$ said framework structure being microporous in which the pores are uniform and have nominal diameters within the range of about 3 to about 10 Angstroms, an intracrystalline adsorption capacity for water at 4.6 torr and 24° C. of at least 3.5 weight percent, the adsorption and desorption of water being completely reversible while retaining the same essential framework topology in both the hydrated and dehydrated state.

2. Process according to claim 1 wherein the more polar molecular species is water.

* * * * *